(12) United States Patent
Chennareddy et al.

(10) Patent No.: US 10,214,746 B2
(45) Date of Patent: Feb. 26, 2019

(54) SOYBEAN TRANSFORMATION METHOD

(71) Applicant: Dow AgroSciences LLC, Indianapolis, IN (US)

(72) Inventors: Sivarama Reddy Chennareddy, West Lafayette, IN (US); Dayakar Pareddy, Carmel, IN (US); Jayakumar Pon Samuel, Carmel, IN (US); Rodrigo Sarria-Milan, West Lafayette, IN (US); Toby Cicak, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 96 days.

(21) Appl. No.: 14/505,060

(22) Filed: Oct. 2, 2014

(65) Prior Publication Data

US 2015/0099648 A1      Apr. 9, 2015

Related U.S. Application Data

(60) Provisional application No. 61/886,945, filed on Oct. 4, 2013.

(51) Int. Cl.
C12N 15/82       (2006.01)

(52) U.S. Cl.
CPC .............. *C12N 15/8201* (2013.01)

(58) Field of Classification Search
None
See application file for complete search history.

(56) References Cited

U.S. PATENT DOCUMENTS

| | | | |
|---|---|---|---|
| 5,830,728 A * | 11/1998 | Christou ............ | C12N 15/8207 435/320.1 |
| 5,914,451 A * | 6/1999 | Martinell ................. | A01H 1/04 435/415 |
| 6,384,301 B1 | 5/2002 | Martinell et al. | |
| 2002/0157139 A1 | 10/2002 | Martinell et al. | |
| 2006/0179511 A1 | 8/2006 | Chomet et al. | |
| 2006/0218660 A1 * | 9/2006 | Dong ................. | C12N 15/8205 800/278 |
| 2008/0153102 A1 * | 6/2008 | Huang ..................... | A01H 3/00 435/5 |
| 2008/0256667 A1 | 10/2008 | Dersch et al. | |

FOREIGN PATENT DOCUMENTS

WO      WO 1996/04392 A2      2/1996
WO      00/42207      7/2000

OTHER PUBLICATIONS

Subramanian et al (RNA Interference of Soybean Isoflavone Synthase Genes Leads to Silencing in Tissues Distal to the Transformation Site and to Enhanced Susceptibility to Phytophthora sojae. Plant Physiology, Apr. 2005, vol. 137, pp. 1345-1353).*
Zhang et al (The use of glufosinate as a selective agent in Agrobacterium-mediated transformation of soybean. Plant Cell, Tissue and Organ Culture 56: 37-46, 1999).*
Rao et al (Non-antibiotic selection systems for soybean somatic embryos: the lysine analog aminoethyl-cysteine as a selection agent. BMC Biotechnology. 9:94, Jan. 17, 2009).*
Christou, P et al., "Prediction of Germ-line Transformation Events in Chimeric RO Transgenic Soybean Plantlets Using Tissue-Specific Expression Patterns.", The Plant Journal., (1992), vol. 2, No. 3, p. 283-290.
International Search Report PCT/US14/58764 dated Jan. 7, 2015 pp. 1-3.
International Preliminary Report on Patentability PCT/US2014/058764 dated Apr. 5, 2016 pp. 1-6.
Liu et al., "Efficient *Agrobacterium tumefaciens*-mediated transformation of soybeans using an embryonic tip regeneration system," Planta (2004) 219: 1042-1049.
Vermeulen et al., "*Agrobacterium* mediated transfer of a mutant *Arabidopsis* acetolactate synthase gene confers resistance to chlorsulfuron in chicory (*Cichorium intybus* L.)," Plant Cell Reports 91992) 11:243-247.
Yamada et al., "Cotyledonary node pre-wounding with a micro-brush increased frequency of *Agrobacterium*-mediated transformation in soybean," Plant Biotechnology 27, 217-220 (2010).
Extended European Search Report, prepared for EP Application No. 14850319.6, dated Feb. 24, 2017.

* cited by examiner

*Primary Examiner* — Medina A Ibrahim
*Assistant Examiner* — Wayne Zhong
(74) *Attorney, Agent, or Firm* — Barnes & Thornburg LLP

(57) ABSTRACT

The present disclosure relates in part to a method for identifying a soybean germline transformant from a population of soybean transformants by incorporating a selection agent within rooting medium used in tissue culture during the soybean transformation process. The soybean germline transformants are selected from a population of soybean transformants which are comprised of a combination of non-germline and germline soybean transformants. The soybean non-germline transformants are identified and eliminated early in the transformation process. The soybean germline transformants are identified and selected for culturing into mature soybean plants. The method is readily applicable for screening and obtaining a soybean germline transformant at an early stage in the soybean transformation process.

25 Claims, 6 Drawing Sheets
Specification includes a Sequence Listing.

L1 layer Transformed:
Non-germline event
YFP expression in epidermal cells only

L2 & L3 layers Transformed:
Germline event
YFP expression in epidermal cells
and core tissue Transgene in Cortex          Rooting under selection

SEQUENCE LISTING

```
<160> NUMBER OF SEQ ID NOS: 2

<210> SEQ ID NO 1
<211> LENGTH: 2783
<212> TYPE: DNA
<213> ORGANISM: Artificial Sequence
<220> FEATURE:
<223> OTHER INFORMATION: First PTU of pDAB 9381 comprising AtUbi10
      Promoter :: yfp :: ORF 23 3'UTR

<400> SEQUENCE: 1
gtcgacctgc aggtcaacgg atcaggatat tcttgtttaa gatgttgaac tctatggagg      60
tttgtatgaa ctgatgatct aggaccggat aagttccctt cttcatagcg aacttattca     120
aagaatgttt tgtgtatcat tcttgttaca ttgttattaa tgaaaaaata ttattggtca     180
ttggactgaa cacgagtgtt aaatatggac caggccccaa ataagatcca ttgatatatg     240
aattaaataa caagaataaa tcgagtcacc aaaccacttg cctttttttaa cgagacttgt     300 tcaccaactt gatacaaaag tcattatcct atgcaaatca ataatcatac aaaaatatcc     360
```

```
aataacacta aaaaattaaa agaaatggat aatttcacaa tatgttatac gataaagaag    420
ttacttttcc aagaaattca ctgattttat aagcccactt gcattagata aatggcaaaa    480
aaaaacaaaa aggaaaagaa ataaagcacg aagaattcta gaaaatacga aatacgcttc    540
aatgcagtgg gacccacggt tcaattattg ccaattttca gctccaccgt atatttaaaa    600
aataaaacga taatgctaaa aaaatataaa tcgtaacgat cgttaaatct caacggctgg    660
atcttatgac gaccgttaga aattgtggtt gtcgacgagt cagtaataaa cggcgtcaaa    720
gtggttgcag ccggcacaca cgagtcgtgt ttatcaactc aaagcacaaa tacttttcct    780
caacctaaaa ataaggcaat tagccaaaaa caactttgcg tgtaaacaac gctcaataca    840
cgtgtcattt tattattagc tattgcttca ccgccttagc tttctcgtga cctagtcgtc    900
ctcgtctttt cttcttcttc ttctataaaa caatacccaa agcttcttct tcacaattca    960
gatttcaatt tctcaaaatc ttaaaaactt tctctcaatt ctctctaccg tgatcaaggt   1020
aaatttctgt gttccttatt ctctcaaaat cttcgatttt gttttcgttc gatcccaatt   1080
tcgtatatgt tctttggttt agattctgtt aatcttagat cgaagacgat tttctgggtt   1140
tgatcgttag atatcatctt aattctcgat tagggtttca taaatatcat ccgatttgtt   1200
caaataattt gagttttgtc gaataattac tcttcgattt gtgatttcta tctagatctg   1260
gtgttagttt ctagtttgtg cgatcgaatt tgtcgattaa tctgagtttt tctgattaac   1320
agagatctcc atgtcatctg gagcacttct ctttcatggg aagattcctt acgttgtgga   1380
gatggaaggg aatgttgatg gccacacctt tagcatacgt gggaaaggct acggagatgc   1440
ctcagtggga aaggtatgtt tctgcttcta cctttgatat atatataata attatcacta   1500
attagtagta atatagtatt tcaagtattt ttttcaaaat aaaagaatgt agtatatagc   1560
tattgctttt ctgtagttta taagtgtgta tattttaatt tataacttttt ctaatatatg   1620 accaaaacat ggtgatgtgc aggttgatgc acaattcatc tgtactaccg gagatgttcc   1680
tgtgccttgg agcacacttg tcaccactct cacctatgga gcacagtgct ttgccaagta   1740
tggtccagag ttgaaggact tctacaagtc ctgtatgcca gatggctatg tgcaagagcg   1800
cacaatcacc tttgaaggag atggcaactt caagactagg gctgaagtca cctttgagaa   1860
tgggtctgtc tacaataggg tcaaactcaa tggtcaaggc ttcaagaaag atggtcacgt   1920
gttgggaaag aacttggagt tcaacttcac tcccccactgc ctctacatct ggggagacca   1980
agccaaccac ggtctcaagt cagccttcaa gatatgtcat gagattactg gcagcaaagg   2040
cgacttcata gtggctgacc acacccagat gaacactccc attggtggag gtccagttca   2100
tgttccagag tatcatcata tgtcttacca tgtgaaactt tccaaagatg tgacagacca   2160
cagagacaac atgagcttga agaaactgt cagagctgtt gactgtcgca agacctacct   2220
ttgagtagtt agcttaatca cctagagctc ggtcaccagc ataattttta ttaatgtact   2280
aaattactgt tttgttaaat gcaattttgc tttctcggga ttttaatatc aaaatctatt   2340
tagaaataca caatatttg ttgcaggctt gctggagaat cgatctgcta tcataaaaat    2400
tacaaaaaaa tttatttgc ctcaattatt ttaggattgg tattaaggac gcttaaatta    2460
tttgtcgggt cactacgcat cattgtgatt gagaagatca gcgatacgaa atattcgtag   2520
tactatcgat aatttatttg aaaattcata agaaaagcaa acgttacatg aattgatgaa   2580
acaatacaaa gacagataaa gccacgcaca tttaggtat tggccgagat tactgaatat    2640
tgagtaagat cacggaattt ctgacaggag catgtcttca attcagccca aatggcagtt   2700
```

```
gaaatactca aaccgcccca tatgcaggag cggatcattc attgtttgtt tggttgcctt    2760
tgccaacatg ggagtccaag gtt                                             2783

<210> SEQ ID NO 2
<211> LENGTH: 1828
<212> TYPE: DNA
<213> ORGANISM: Artificial Sequence
<220> FEATURE:
<223> OTHER INFORMATION: Second PTU of pDAB9381 comprising CsVMV
      promoter :: pat :: Orf1 3'UTR

<400> SEQUENCE: 2
ccagaaggta attatccaag atgtagcatc aagaatccaa tgtttacggg aaaaactatg      60
gaagtattat gtaagctcag caagaagcag atcaatatgc ggcacatatg caacctatgt     120
tcaaaaatga agaatgtaca gatacaagat cctatactgc cagaatacga agaagaatac     180
gtagaaattg aaaagaaga accaggcgaa gaaaagaatc ttgaagacgt aagcactgac      240
gacaacaatg aaaagaagaa gataaggtcg gtgattgtga agagacata gaggacacat      300 gtaaggtgga aatgtaagg gcggaaagta accttatcac aaaggaatct tatcccccac      360
tacttatcct tttatatttt tccgtgtcat ttttgccctt gagttttcct atataaggaa     420
ccaagttcgg catttgtgaa aacaagaaaa aatttggtgt aagctatttt ctttgaagta     480
ctgaggatac aacttcagag aaatttgtaa gtttgtaggt accagatctg gatcccaaac     540
catgtctccg gagaggagac cagttgagat taggccagct acagcagctg atatggccgc     600
ggtttgtgat atcgttaacc attacattga gacgtctaca gtgaacttta ggacagagcc     660
acaaacacca caagagtgga ttgatgatct agagaggttg caagatagat acccttggtt     720
ggttgctgag gttgagggtg ttgtggctgg tattgcttac gctgggccct ggaaggctag     780
gaacgcttac gattggacag ttgagagtac tgtttacgtg tcacataggc atcaaaggtt     840
gggcctagga tctacattgt acacacattt gcttaagtct atggaggcgc aaggttttaa     900
gtctgtggtt gctgttatag gccttccaaa cgatccatct gttaggttgc atgaggcttt     960
gggatacaca gcccgggta cattgcgcgc agctggatac aagcatggtg gatggcatga    1020
tgttggtttt tggcaaaggg attttgagtt gccagctcct ccaaggccag ttaggccagt    1080
tacccaaatc tgagtagtta gcttaatcac ctagagctcg atcggcggca atagcttctt    1140
agcgccatcc cggttgatc ctatctgtgt tgaaatagtt gcggtgggca aggctctctt     1200
tcagaaagac aggcggccaa aggaacccaa ggtgaggtgg gctatggctc tcagttcctt    1260
gtggaagcgc ttggtctaag gtgcagaggt gttagcggga tgaagcaaaa gtgtccgatt    1320
gtaacaagat atgttgatcc tacgtaagga tattaaagta tgtattcatc actaatataa    1380
tcagtgtatt ccaatatgta ctacgatttc caatgtcttt attgtcgccg tatgtaatcg    1440
gcgtcacaaa ataatccccg tgactttct tttaatccag gatgaaataa tatgttatta     1500 taattttgc gatttggtcc gttataggaa ttgaagtgtg cttgaggtcg tcgccacca      1560 ctcccatttc ataattttac atgtatttga aaaataaaaa tttatggtat tcaatttaaa    1620
cacgtatact tgtaaagaat gatatcttga aagaaatata gtttaaatat ttattgataa    1680
aataacaagt caggtattat agtccaagca aaaacataaa tttattgatg caagtttaaa    1740
ttcagaaata tttcaataac tgattatatc agctggtaca ttgccgtaga tgaaagactg    1800
agtgcgatat tatggtgtaa tacatagg                                       1828
```

SOYBEAN TRANSFORMATION METHOD

CROSS REFERENCE TO RELATED APPLICATIONS

This application claims priority under 35 U.S.C. § 119(e) of U.S. Provisional Application No. 61/886,945, filed Oct. 4, 2013, which is hereby incorporated by reference in its entirety

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 8 KB ACII (Text) file named "231578_ST25" created on Sep. 30, 2014.

FIELD OF THE INVENTION

The present disclosure relates to a method for transforming soybean cells. In various aspects, soybean germline transformants are produced and identified from a population of soybean transformants comprising non-germline and germline transformants. Accordingly, the soybean non-germline transformants may be identified and eliminated early in the transformation process. The soybean germline transformants are detected by identifying transformed soybean shoots that produce viable roots, and then may be selected for culturing into mature soybean plants. In various embodiments, the method is readily applicable for screening and obtaining a soybean germline transformant at an early stage in the transformation process.

BACKGROUND OF THE INVENTION

Over the last thirty years, improvements to transformation methodologies have resulted in increased transformation efficiency of soybeans. As a result, agronomically valuable traits may be routinely incorporated into the soybean genome. For example, new transgenic soybean products, such as Enlist™ soybeans, are commercially available throughout the world and offer improved solutions for ever-increasing challenges caused by weeds. Such innovative products would not be possible but for development and improvement of soybean transformation methodologies. New and improved soybean transformation methodologies that can be utilized to detect and select soybean germline transformants at early stages within the soybean transformation process are important for continuing to improve the efficiency of the soybean transformation process.

The early identification and selection of soybean germline transformants in a transformation process is highly desirable because these soybean germline transformants comprise a stably integrated transgene which is heritable in subsequent generations. However, due to the relative inefficiencies of the transformation process, large numbers of transformants must be produced in order to identify and to select-desirable soybean germline transformants from the undesirable soybean non-germline transformants. On average, about 40 to 70 percent of all isolated transformants are undesirable soybean non-germline transformants, such as chimeric or soybean non-germline transformants, which must be "culled" (i.e., discarded) in favor of the desirable soybean germline transformants. However, using traditional methods, the process of culling occurs only after the transformants are maintained throughout the transformation process and have advanced to maturity. Using traditional methods, the maintenance of undesirable transformants, such as non-germline soybean transformants, results in an inefficient use of resources and an undesirable increase in cost expended to produce transgenic plants from the non-germline transformants. Such costs exceed pecuniary concerns and include the use of scientists' time, materials, and laboratory space. The present disclosure provides methods that exhibit desirable properties and provides related advantages for identification and selection of soybean germline transformants. The present disclosure demonstrates that the identification and selection of soybean germline transformants at the early stages of the plant transformation can be accomplished using a selective rooting medium containing a selection agent. Through use of the selective rooting medium, undesirable chimeric or soybean non-germline transformants can be culled without the requirement of maintenance throughout the transformation process and without advancing through maturity. As a result, the production of transgenic plants may be more efficient, and an improvement in allocating resources to produce transgenic plants may be realized.

The foregoing examples of the related art and limitations related therewith are intended to be illustrative and not exclusive. Other limitations of the related art will become apparent to those of skill in the art upon a reading of the specification.

BRIEF SUMMARY OF THE INVENTION

Disclosed herein is a method of identifying shoots created from soybean germline transformants. As an embodiment, a population of cells of a soybean plant are transformed with a transgene. In a subsequent embodiment, the population of transformed cells are regenerated into shoots. In a further embodiment, shoots are produced from the population of cells and isolated. In an embodiment, the shoots are contacted with a selective rooting medium, wherein the selective rooting medium contains glufosinate. In yet another embodiment, the isolated regenerated shoots are cultivated in the presence of glufosinate, wherein the isolated regenerated shoots produced by the transformed germline cells create viable roots in the presence of glufosinate, and the isolated regenerated shoots produced by the transformed non-germline cells do not create viable roots in the presence of glufosinate. In a subsequent embodiment, the shoots created from the soybean germline transformants are identified by detecting whether or not the shoot creates viable roots.

In another aspect, disclosed herein is a method of identifying shoots created from soybean germline transformants. In an embodiment, a population of cells of a soybean plant are transformed with a transgene, wherein the population of transformed cells comprises transformed germline cells and transformed non-germline cells. In a further embodiment, shoots are regenerated from the population of transformed cells. In yet another embodiment, shoots produced by the population of transformed cells are isolated. In a subsequent embodiment, the isolated regenerated shoots are subjected to a selective rooting medium, wherein the subjected isolated regenerated shoots produced by the transformed germline cells create viable roots, and the subjected isolated regenerated shoots produced by the transformed non-germline cells do not create viable roots. In a further embodiment, the shoots created from soybean germline transformants are identified by detecting whether or not the shoot creates viable roots.

In a further aspect, disclosed herein is a method of identifying a soybean germline transformant. In an embodiment, a population of cells of a soybean plant are transformed with a transgene. In a subsequent embodiment, shoots are regenerated from the transformed population of cells of a soybean plant comprising the transgene. In a further embodiment the regenerated shoot is isolated from the transformed population of cells of a soybean plant, wherein the transformed population of cells of a soybean plant comprise the transgene. In an additional embodiment, the isolated regenerated shoot is contacted with a rooting medium, wherein the rooting medium comprises one or more selection agents. In a final embodiment, the isolated regenerated shoot is cultured on the rooting medium so as to produce viable roots, wherein the production of viable roots identifies the soybean germline transformant.

In another aspect, disclosed herein is a method for producing a soybean germline transformant or a soybean non-germline transformant, the method comprising the step of culturing one or more regenerated shoots in a rooting medium comprising a selection agent, wherein the one or more regenerated shoots are isolated from a population of soybean cells transformed with a transgene, wherein the one or more regenerated shoots comprising a soybean non-germline transformant does not produce viable roots and the one or more regenerated shoots comprising a soybean germline transformant produces viable roots.

In a further aspect, disclosed herein is a method for preventing viable root production from a population of transformed non-germline soybean cells. In an embodiment, a population of soybean cells are transformed with a transgene, wherein the transformed population of soybean cells comprises a population of transformed germline soybean cells and a population of transformed non-germline soybean cells. In a further embodiment, one or more shoots are regenerated from the transformed population of soybean cells. In a subsequent embodiment, the one or more regenerated shoots produced from the transformed population of soybean cells are isolated. In an embodiment, the one or more isolated regenerated shoots are contacted with a rooting medium, wherein the rooting medium comprises a selection agent. In yet another embodiment, the one or more isolated regenerated shoots are cultured on the rooting medium, wherein the one or more isolated regenerated shoots of the transformed germline soybean cells produce viable roots in the presence of the rooting medium comprising a selection agent, and the one or more isolated regenerated shoots of the transformed non-germline soybean cells prevent viable root production in the presence of the rooting medium comprising a selection agent.

In addition to the exemplary aspects and embodiments described above, further aspects and embodiments will become apparent by study of the following descriptions.

DETAILED DESCRIPTION

I. Overview

Figure 1:
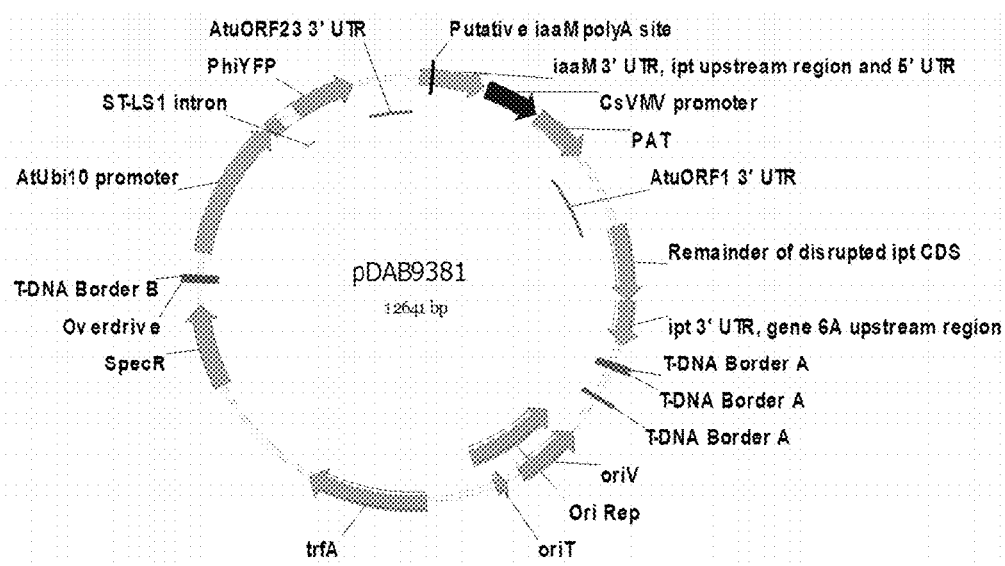
FIG. 1 illustrates a plasmid map of pDAB9381.

The present disclosure provides, in various aspects, methods that provide for identification and advancement of soybean germline transformants and for elimination or culling of soybean non-germline transformants. Briefly, soybean cells are transformed, followed by regeneration of shoots from the transformants and cultivation in a rooting medium comprising a selection agent. According to the disclosed methods, the resultant soybean transformants comprising a stably integrated transgene may be identified and selected early in the soybean transformation process. Soybean germline transformants may be identified according to expression of a transgene within the core (e.g., L2 and L3) layers of the soybean shoots. Identified soybean germline transformants may then be selected and cultured into mature soybean plants. In addition, soybean non-germline transformants may be identified using the disclosed methods and may be culled from the transformation process at an earlier stage compared to traditional methods. As such, soybean plant transformants can be cultivated in a rooting medium comprising a selection agent to identify and select specific transformants which have a transgene inserted within the germline tissues.

The development of the soybean transformation method that can be utilized for identifying soybean germline transformants at an early stage in the soybean transformation process is favorable as the method can improve the efficiency of the soybean transformation process.

Such a method is disclosed in this application, a method of identifying shoots created from soybean germline transformants is provided. The method comprises a) transforming a population of cells of a soybean plant with a transgene, wherein the transformed cell population comprises transformed germline cells and transformed non-germline cells; b) regenerating shoots from the population of transformed cells; c) isolating the shoots produced by the population of transformed cells; d) contacting the shoots with a selective rooting medium, wherein the selective rooting medium contains glufosinate; e) cultivating the isolated regenerated shoots in the presence of glufosinate, wherein (i) the isolated regenerated shoots produced by the transformed germline cells create viable roots in the presence of glufosinate, and (ii) the isolated regenerated shoots produced by the transformed non-germline cells do not create viable roots in the presence of glufosinate; and f) identifying the shoots created from soybean germline transformants by detecting whether or not the shoot creates viable roots.

In another embodiment of the present disclosure, a second method of identifying shoots created from soybean germline transformants is provided. The method comprises a) transforming a population of cells of a soybean plant with a transgene, wherein the population of transformed cells comprises transformed germline cells and transformed non-germline cells; b) regenerating shoots from the population of transformed cells; c) isolating the shoots produced by the population of transformed cells; d) subjecting the isolated regenerated shoots to a selective rooting medium, wherein (i) the subjected isolated regenerated shoots produced by the transformed germline cells create viable roots, and (ii) the subjected isolated regenerated shoots produced by the transformed non-germline cells do not create viable roots; and e) identifying the shoots created from soybean germline transformants by detecting whether or not the shoot creates viable roots.

In yet another embodiment of the present disclosure, a method for identifying a soybean germline transformant is provided. The method comprises a) transforming a population of cells of a soybean plant with a transgene; b) regenerating a shoot from the transformed population of cells of a soybean plant comprising the transgene; c) isolating the regenerated shoot from the transformed population of cells of a soybean plant, wherein the transformed population of cells of a soybean plant comprise the transgene; d) contacting the isolated regenerated shoot with a rooting medium, wherein the rooting medium comprises one or more selection agents; and e) culturing the isolated regenerated shoot on the rooting medium so as to produce viable roots, wherein the production of viable roots identifies the soybean germline transformant.

In another embodiment of the present disclosure, a method of producing a soybean germline transformant or a soybean non-germline transformant is provided. The method comprises the step of culturing one or more regenerated shoots in a rooting medium comprising a selection agent, wherein the one or more regenerated shoots are isolated from a population of soybean cells transformed with a transgene, wherein the one or more regenerated shoots comprising a soybean non-germline transformant does not produce viable roots and the one or more regenerated shoots comprising a soybean germline transformant produces viable roots.

In yet another embodiment of the present disclosure, a method for preventing viable root production from a population of transformed non-germline soybean cells is provided. The method comprises the steps of a) transforming a population of soybean cells with a transgene, wherein the transformed population of soybean cells comprises a population of transformed germline soybean cells and a population of transformed non-germline soybean cells; b) regenerating one or more shoots from the transformed population of soybean cells; c) isolating the one or more regenerated shoots produced from the transformed population of soybean cells; d) contacting the one or more isolated regenerated shoots with a rooting medium, wherein the rooting medium comprises a selection agent; and e) culturing the one or more isolated regenerated shoots on the rooting medium, wherein (i) the one or more isolated regenerated shoots of the transformed germline soybean cells produce viable roots in the presence of the rooting medium comprising a selection agent, and (ii) the one or more isolated regenerated shoots of the transformed non-germline soybean cells prevent viable root production in the presence of the rooting medium comprising a selection agent.

In another embodiment, the disclosed method utilizes the incorporation of the selection agent, glufosinate, within rooting medium for the identification and selection of transformants comprising a transgene inserted within soybean germline tissues. In various embodiments the incorporation of the selection agent, glufosinate, at specific concentrations in the rooting medium of soybean tissue explants (e.g., split seed, apical meristem, etc.) undergoing organogenesis for the identification and selection of soybean transformants comprising a transgene inserted within the germline tissue are disclosed for the first time. In an embodiment, the incorporation of glufosinate in rooting stage medium of soybean tissues transformed using an organogenic transformation system was found not to be inhibitory, and did not interfere with plantlet development. In an embodiment, organogenic transformation systems may comprise *Agrobacterium*-mediated transformation of cotyledonary nodes, half seed or split seed transformation, and particle bombardment of shoot meristems. Yet in another embodiment, the disclosed method allows for phenotypic selection of plantlets based on visual observations of root phenotypes to identify and select germline transformants from non-germline transformants.

II. Terms

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of an embodiment of the disclosure are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as disclosed in the application.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, an "isolated" biological component (such as a nucleic acid or polypeptide) means a component that has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

As used herein, the terms "polynucleotide," "nucleic acid," and "nucleic acid molecule" are used interchangeably, and may encompass a singular nucleic acid; plural nucleic acids; a nucleic acid fragment, variant, or derivative thereof; and nucleic acid construct (e.g., messenger RNA (mRNA) and plasmid DNA (pDNA)). A polynucleotide or nucleic acid may contain the nucleotide sequence of a full-length cDNA sequence, or a fragment thereof, including untranslated 5' and/or 3' sequences and coding sequence(s). A polynucleotide or nucleic acid may be comprised of any polyribonucleotide or polydeoxyribonucleotide, which may include unmodified ribonucleotides or deoxyribonucleotides or modified ribonucleotides or deoxyribonucleotides. For example, a polynucleotide or nucleic acid may be comprised of single- and double-stranded DNA; DNA that is a mixture of single- and double-stranded regions; single- and double-stranded RNA; and RNA that is mixture of single- and double-stranded regions. Hybrid molecules comprising DNA and RNA may be single-stranded, double-stranded, or a mixture of single- and double-stranded regions. The foregoing terms also include chemically, enzymatically, and metabolically modified forms of a polynucleotide or nucleic acid.

It is understood that a specific DNA refers also to the complement thereof, the sequence of which is determined according to the rules of deoxyribonucleotide base-pairing.

As used herein, the term "gene" refers to a nucleic acid that encodes a functional product (RNA or polypeptide/protein). A gene may include regulatory sequences preceding (5' non-coding sequences) and/or following (3' non-coding sequences) the sequence encoding the functional product.

As used herein, the term "coding sequence" refers to a nucleic acid sequence that encodes a specific amino acid sequence. A "regulatory sequence" refers to a nucleotide sequence located upstream (e.g., 5' non-coding sequences), within, or downstream (e.g., 3' non-coding sequences) of a coding sequence, which influence the transcription, RNA processing or stability, or translation of the associated coding sequence. Regulatory sequences include, for example and without limitation: promoters; translation leader sequences; introns; polyadenylation recognition sequences; RNA processing sites; effector binding sites; and stem-loop structures.

As used herein, the term "polypeptide" includes a singular polypeptide, plural polypeptides, and fragments thereof. This term refers to a molecule comprised of monomers (amino acids) linearly linked by amide bonds (also known as peptide bonds). The term "polypeptide" refers to any chain or chains of two or more amino acids, and does not refer to a specific length or size of the product. Accordingly, peptides, dipeptides, tripeptides, oligopeptides, protein, amino acid chain, and any other term used to refer to a chain or chains of two or more amino acids, are included within the definition of "polypeptide," and the foregoing terms are used interchangeably with "polypeptide" herein. A polypeptide may be isolated from a natural biological source or produced by recombinant technology, but a specific polypeptide is not necessarily translated from a specific nucleic acid. A polypeptide may be generated in any appropriate manner, including for example and without limitation, by chemical synthesis.

As used herein, the term "native" refers to the form of a polynucleotide, gene or polypeptide that is found in nature with its own regulatory sequences, if present. The term "endogenous" refers to the native form of the polynucleotide, gene or polypeptide in its natural location in the organism or in the genome of the organism.

In contrast, the term "heterologous" refers to a polynucleotide, gene or polypeptide that is not normally found at its location in the reference (host) organism. For example, a heterologous nucleic acid may be a nucleic acid that is normally found in the reference organism at a different genomic location. By way of further example, a heterologous nucleic acid may be a nucleic acid that is not normally found in the reference organism. A host organism comprising a hetereologous polynucleotide, gene or polypeptide may be produced by introducing the heterologous polynucleotide, gene or polypeptide into the host organism. In particular examples, a heterologous polynucleotide comprises a native coding sequence, or portion thereof, that is reintroduced into a source organism in a form that is different from the corresponding native polynucleotide. In particular examples, a heterologous gene comprises a native coding sequence, or portion thereof, that is reintroduced into a source organism in a form that is different from the corresponding native gene. For example, a heterologous gene may include a native coding sequence that is a portion of a chimeric gene including non-native regulatory regions that is reintroduced into the native host. In particular examples, a heterologous polypeptide is a native polypeptide that is reintroduced into a source organism in a form that is different from the corresponding native polypeptide.

A heterologous gene or polypeptide may be a gene or polypeptide that comprises a functional polypeptide or nucleic acid sequence encoding a functional polypeptide that is fused to another genes or polypeptide to produce a chimeric or fusion polypeptide, or a gene encoding the same. Genes and proteins of particular embodiments include specifically exemplified full-length sequences and portions, segments, fragments (including contiguous fragments and internal and/or terminal deletions compared to the full-length molecules), variants, mutants, chimerics, and fusions of these sequences.

As used herein, the term "modification" may refer to a change in a particular reference polynucleotide that results in reduced, substantially eliminated, or eliminated activity of a polypeptide encoded by the reference polynucleotide. A modification may also refer to a change in a reference polypeptide that results in reduced, substantially eliminated, or eliminated activity of the reference polypeptide. Alternatively, the term "modification" may refer to a change in a reference polynucleotide that results in increased or enhanced activity of a polypeptide encoded by the reference polynucleotide, as well as a change in a reference polypeptide that results in increased or enhanced activity of the reference polypeptide. Changes such as the foregoing may be made by any of several methods well-known in the art including, for example and without limitation: deleting a portion of the reference molecule; mutating the reference molecule (e.g., via spontaneous mutagenesis, via random mutagenesis, via mutagenesis caused by mutator genes, and via transposon mutagenesis); substituting a portion of the reference molecule; inserting an element into the reference molecule; down-regulating expression of the reference molecule; altering the cellular location of the reference molecule; altering the state of the reference molecule (e.g., via methylation of a reference polynucleotide, and via phosphorylation or ubiquitination of a reference polypeptide); removing a cofactor of the reference molecule; introduction of an antisense RNA/DNA targeting the reference molecule; introduction of an interfering RNA/DNA targeting the reference molecule; chemical modification of the reference molecule; covalent modification of the reference molecule; irradiation of the reference molecule with UV radiation or X-rays; homologous recombination that alters the reference molecule; mitotic recombination that alters the reference molecule; replacement of the promoter of the reference molecule; and/or combinations of any of the foregoing.

Guidance in determining which nucleotides or amino acid residues may be modified in a specific example may be found by comparing the sequence of the reference polynucleotide or polypeptide with that of homologous (e.g., homologous yeast or bacterial) polynucleotides or polypeptides, and maximizing the number of modifications made in regions of high homology (conserved regions) or consensus sequences.

The term "promoter" refers to a DNA sequence capable of controlling the expression of a nucleic acid coding sequence or functional RNA. In examples, the controlled coding sequence is located 3' to a promoter sequence. A promoter may be derived in its entirety from a native gene, a promoter may be comprised of different elements derived from different promoters found in nature, or a promoter may even comprise synthetic DNA segments. It is understood by those skilled in the art that different promoters can direct the expression of a gene in different tissues or cell types, or at different stages of development, or in response to different environmental or physiological conditions. Examples of all of the foregoing promoters are known and used in the art to control the expression of heterologous nucleic acids. Promoters that direct the expression of a gene in most cell types at most times are commonly referred to as "constitutive promoters." Furthermore, while those in the art have (in many cases unsuccessfully) attempted to delineate the exact boundaries of regulatory sequences, it has come to be understood that DNA fragments of different lengths may have identical promoter activity. The promoter activity of a particular nucleic acid may be assayed using techniques familiar to those in the art.

The term "operably linked" refers to an association of nucleic acid sequences on a single nucleic acid, wherein the function of one of the nucleic acid sequences is affected by another. For example, a promoter is operably linked with a coding sequence when the promoter is capable of effecting the expression of that coding sequence (e.g., the coding sequence is under the transcriptional control of the promoter). A coding sequence may be operably linked to a regulatory sequence in a sense or antisense orientation.

The term "expression," as used herein, may refer to the transcription and stable accumulation of sense (mRNA) or antisense RNA derived from a DNA. Expression may also refer to translation of mRNA into a polypeptide. As used herein, the term "overexpression" refers to expression that is higher than endogenous expression of the same gene or a related gene. Thus, a heterologous gene is "overexpressed" if its expression is higher than that of a comparable endogenous gene.

As used herein, the term "transformation" or "transforming" refers to the transfer and integration of a nucleic acid or fragment thereof into a host organism, resulting in genetically stable inheritance. Host organisms containing a transforming nucleic acid are referred to as "transgenic," "recombinant," or "transformed" organisms. Known methods of transformation include, for example: *Agrobacterium tumefaciens*- or *A. rhizogenes*-mediated transformation; calcium phosphate transformation; polybrene transformation; protoplast fusion; electroporation; ultrasonic methods (e.g., sonoporation); liposome transformation; microinjection; transformation with naked DNA; transformation with plasmid vectors; transformation with viral vectors; biolistic transformation (microparticle bombardment); silicon carbide WHISKERS-mediated transformation; aerosol beaming; and PEG-mediated transformation.

As used herein, the term "introduced" (in the context of introducing a nucleic acid into a cell) includes transformation of a cell, as well as crossing a plant comprising the nucleic acid with a second plant, such that the second plant contains the nucleic acid, as may be performed utilizing conventional plant breeding techniques. Such breeding techniques are known in the art. For a discussion of plant breeding techniques, see Poehlman (1995) Breeding Field Crops, 4th Edition, AVI Publication Co., Westport Conn.

Backcrossing methods may be used to introduce a nucleic acid into a plant. This technique has been used for decades to introduce traits into plants. An example of a description of backcrossing (and other plant breeding methodologies) can be found in, for example, Poelman (1995), supra; and Jensen (1988) Plant Breeding Methodology, Wiley, New York, N.Y. In an exemplary backcross protocol, an original plant of interest (the "recurrent parent") is crossed to a second plant (the "non-recurrent parent") that carries the a nucleic acid be introduced. The resulting progeny from this cross are then crossed again to the recurrent parent, and the process is repeated until a converted plant is obtained, wherein essentially all of the desired morphological and physiological characteristics of the recurrent parent are recovered in the converted plant, in addition to the nucleic acid from the non-recurrent parent.

The terms "plasmid" and "vector," as used herein, refer to an extra chromosomal element that may carry one or more gene(s) that are not part of the central metabolism of the cell. Plasmids and vectors typically are circular double-stranded DNA molecules. However, plasmids and vectors may be linear or circular nucleic acids, of a single- or double-stranded DNA or RNA, and may be derived from any source, in which a number of nucleotide sequences have been joined or recombined into a unique construction that is capable of introducing a promoter fragment and a coding DNA sequence along with any appropriate 3' untranslated sequence into a cell. In examples, plasmids and vectors may comprise autonomously replicating sequences, genome integrating sequences, and/or phage or nucleotide sequences.

Polypeptide and "protein" are used interchangeably herein and include a molecular chain of two or more amino acids linked through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be synthesized, or expressed recombinantly using known protein engineering techniques. In addition, inventive fusion proteins can be derivatized as described herein by well-known organic chemistry techniques.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

III. Embodiments of the Present Invention

In one embodiment of the present disclosure, a method of identifying shoots created from soybean germline transformants is provided. The method comprises a) transforming a population of cells of a soybean plant with a transgene, wherein the transformed cell population comprises transformed germline cells and transformed non-germline cells; b) regenerating shoots from the population of transformed cells; c) isolating the shoots produced by the population of transformed cells; d) contacting the shoots with a selective rooting medium, wherein the selective rooting medium contains glufosinate; e) cultivating the isolated regenerated shoots in the presence of glufosinate, wherein (i) the isolated regenerated shoots produced by the transformed germline cells create viable roots in the presence of glufosinate, and (ii) the isolated regenerated shoots produced by the transformed non-germline cells do not create viable roots in the presence of glufosinate; and f) identifying the shoots created from soybean germline transformants by detecting whether or not the shoot creates viable roots.

In this embodiment, a population of cells of a soybean plant is transformed with a transgene by any of several transformation methods known in the art. Nucleic acids introduced into a soybean plant cell may be used to confer desired agronomic traits in soybean. A wide variety of soybean plants and plant cell systems may be engineered for the desired physiological and agronomic characteristics described herein using a nucleic acid and various transformation methods. Embodiments herein may use any of the known methods for the transformation of plants (and production of genetically modified plants) that are known in the art. Numerous methods for plant transformation have been developed, including biological and physical transformation protocols for dicotyledenous plants, as well as monocotyledenous plants (See, e.g., Goto-Fumiyuki et al. (1999) Nat. Biotechnol. 17:282-6; Mild et al. (1993) *Methods in Plant Molecular Biology and Biotechnology* (Glick, B. R. and Thompson, J. E., Eds.), CRC Press, Inc., Boca Raton, Fla., pp. 67-88). In addition, vectors and in vitro culture methods for plant cell and tissue transformation and regeneration of plants are described, for example, in Gruber et al. (1993), supra, at pp. 89-119.

Plant transformation methodologies available for introducing a nucleic acid into a plant host cell include, for example and without limitation: transformation with disarmed T-DNA using *Agrobacterium tumefaciens* or *A. rhizogenes* as the transformation agent; calcium phosphate transfection; polybrene transformation; protoplast fusion; electroporation (D'Halluin et al. (1992) Plant Cell 4:1495-505); ultrasonic methods (e.g., sonoporation); liposome transformation; microinjection; contact with naked DNA; contact with plasmid vectors; contact with viral vectors; biolistics (e.g., DNA particle bombardment (see, e.g., Klein et al. (1987) Nature 327:70-3) and microparticle bombardment (Sanford et al. (1987) Part. Sci. Technol. 5:27; Sanford (1988) Trends Biotech. 6:299, Sanford (1990) Physiol. Plant 79:206; and Klein et al. (1992) Biotechnology 10:268); silicon carbide WHISKERS™-mediated transformation (Kaeppler et al. (1990) Plant Cell Rep. 9:415-8); nanoparticle transformation (see, e.g., U.S. Patent Publication No. US2009/0104700A1); aerosol beaming; and polyethylene glycol (PEG)-mediated uptake. In specific examples, a transgene may be introduced directly into the genomic DNA of a soybean plant cell via one of the previously described transformation protocols.

A widely utilized method for introducing a gene expression cassette comprising a transgene into a plant is based on the natural transformation system of *Agrobacterium*. Horsch et al. (1985) Science 227:1229. *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado (1991) Crit. Rev. Plant. Sci. 10:1. Details regarding *Agrobacterium* vector systems and methods for *Agrobacterium*-mediated gene transfer are also available in, for example, Gruber et al., supra, Mild et al., supra, Moloney et al. (1989) Plant Cell Reports 8:238, and U.S. Pat. Nos. 4,940,838 and 5,464,763.

If *Agrobacterium* is used for the transformation, the DNA to be inserted typically is cloned into special plasmids, either in an intermediate vector or a binary vector. Intermediate vectors cannot replicate themselves in *Agrobacterium*. The intermediate vector may be transferred into *A. tumefaciens* by means of a helper plasmid (conjugation). The Japan Tobacco Superbinary system is an example of such a system (reviewed by Komari et al. (2006) *Methods in Molecular Biology* (K. Wang, ed.) No. 343; *Agrobacterium Protocols*, $2^{nd}$ Edition, Vol. 1, Humana Press Inc., Totowa, N.J., pp. 15-41; and Komori et al. (2007) Plant Physiol. 145:1155-60). Binary vectors can replicate themselves both in *E. coli* and in *Agrobacterium*. Binary vectors comprise a selection marker gene and a linker or polylinker which are framed by the right and left T-DNA border regions. They can be transformed directly into *Agrobacterium* (Holsters, 1978). The *Agrobacterium* comprises a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the gene expression cassette and adjacent marker into the plant cell DNA when the cell is infected by the bacteria using a binary T DNA vector (Bevan (1984) Nuc. Acid Res. 12:8711-21) or the co-cultivation procedure (Horsch et al. (1985) Science 227:1229-31). Generally, the *Agrobacterium* transformation system is used to engineer dicotyledonous plants. Bevan et al. (1982) Ann. Rev. Genet 16:357-84; Rogers et al. (1986) Methods Enzymol. 118:627-41. The *Agrobacterium* transformation system may also be used to transform, as well as transfer, nucleic acids to monocotyledonous plants and plant cells. See U.S. Pat. No. 5,591,616; Hernalsteen et al. (1984) EMBO J 3:3039-41; Hooykass-Van Slogteren et al. (1984) Nature 311:763-4; Grimsley et al. (1987) Nature 325:1677-9; Boulton et al. (1989) Plant Mol. Biol. 12:31-40; and Gould et al. (1991) Plant Physiol. 95:426-34.

The genetic manipulations of a recombinant host herein may be performed using standard recombinant DNA techniques and screening, and may be carried out in any host cell that is suitable to genetic manipulation. In some embodiments, a recombinant host cell may be any soybean plant or variety suitable for genetic modification and/or recombinant gene expression. In some embodiments, a recombinant host may be a soybean germline transformant plant. Standard recombinant DNA and molecular cloning techniques used here are well-known in the art and are described in, for example and without limitation: Sambrook et al. (1989), supra; Silhavy et al. (1984) *Experiments with Gene Fusions*, Cold Spring Harbor Laboratory Press, Cold Spring Harbor, N.Y.; and Ausubel et al. (1987) *Current Protocols in Molecular Biology*, Greene Publishing Assoc. and Wiley-Interscience, New York, N.Y.

In some embodiments, a soybean plant tissue is transformed via an *Agrobacterium*-mediated method of modified half-seed explants (Paz M., et al., (2005) *Plant Cell Rep.*, 25: 206-213), a cotyledonary node transformation method (Zeng P., et al., (2004), *Plant Cell Rep.*, 22(7): 478-482), or a split seed with partial embryo axis soybean transformation method (U.S. Filing No. 61/739,349). Using any of these methods, or any other known soybean transformation method, the transgene is delivered to soybean plant tissues which comprise the outer mantle tissue (L1 layer) or delivered to underlying tissues located deeper within the plant, such as the core tissues (L2 and L3 layers). The mantle tissue (L1 layer) will divide to form the epidermal and ground tissues which comprise non-germline cells. The core tissues divide to form the meristematic and vascular tissues which comprise germline cells. Only the transgenic events with transformed germline cells can pass the transgene to the next generation.

In this embodiment, the transformed cell population comprises transformed germline cells and transformed non-germline cells. Use of a transgene for transformation of core cells (L2 and L3 layers) which comprise the meristematic and vascular plant cells results in the transformation of a soybean germline cell. The germline cells are capable of regeneration to produce a mature transgenic plant (i.e., germline transformant).

Use of a transgene for transformation of mantle cells (L1 layer) which comprise the ground and dermal plant cells results in the transformation of a soybean non-germline cell. The non-germline cells are not capable of regeneration to produce a mature transgenic plant (i.e., non-germline transformant).

In this embodiment, shoots are regenerated from the population of transformed cells. Plant shoots are well known to a person of ordinary skill in the art, and includes aerial vascular plant parts (including, but not limited to; stems, branches, buds, reproductive organs, leaves, and shoot-derived structures such as stolons, corms, rhizomes or tubers), plant tissues, and plant cells that develop from a seed or cutting.

Transformed soybean plant cells which are produced by any of the above transformation techniques can be cultured to regenerate a mature soybean plant that possesses the transformed genotype, and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) Ann. Rev. of Plant Phys. 38:467-486.

Methodologies for regenerating plants are known to those of ordinary skill in the art and can be found, for example, in: Plant Cell and Tissue Culture, 1994, Vasil and Thorpe Eds. Kluwer Academic Publishers and in: Plant Cell Culture Protocols (Methods in Molecular Biology 111, 1999 Hall Eds Humana Press). Genetically modified soybean plants described herein may be cultured in a fermentation medium or grown in a suitable medium such as soil. In some embodiments, a suitable growth medium for higher plants may be any growth medium for plants, including, but not limited to, soil, sand, any other particulate media that support root growth (e.g., vermiculite, perlite, etc.) or hydroponic culture, as well as suitable light, water and nutritional supplements that facilitate the growth of the higher plant.

In this embodiment, the shoots produced by the population of transformed cells are isolated. As used herein, the term "isolated" or "isolating" refers to the removal of the shoots from other plant structures or tissues so that the removed shoot is substantially free of the other plant structures or tissues. As such, the shoots are devoid of other components, in whole or in part, that the shoots are normally associated with in tissue culture.

In this embodiment, the shoots are contacted with a selective rooting medium, wherein the selective rooting medium contains glufosinate. As used herein, the term "contacted" or "contacting" refers to bringing the isolated shoot in contact with the selective rooting medium. Accordingly, "contacted" or "contacting" may result in a touching of the isolated shoot with the rooting medium so as to bring the isolated shoot in close physical proximity of the rooting medium. Additionally, "contacted" or "contacting" may result in an isolated shoot that is embedded within the rooting medium. As used herein, the term "selective rooting medium" refers to a tissue culture medium comprising basal salts, carbon sources, vitamins, minerals and plant phytohormones. In the embodiments, the plant phytohormones can be provided at varying concentrations or ratios, wherein root tissues develop and proliferate from undifferentiated cells placed upon the selective rooting medium. In the embodiments, the selective rooting medium contains glufosinate. In the embodiments, the selective rooting medium contains 2,4-D.

In this embodiment, the isolated regenerated shoots are cultivated in the presence of glufosinate. As used herein, the term "cultivated" or "cultivating" refers to a plant, plant part, or plant cell purposely grown (increases in cell size, cellular contents, and/or cellular activity) and or propagated (increases in cell numbers via mitosis) under tissue culture conditions. In the embodiment, the isolated regenerated shoots produced by the transformed germline cells create viable roots in the presence of glufosinate. In the embodiment, the isolated regenerated shoots produced by the transformed non-germline cells do not create viable roots in the presence of glufosinate. As used herein, the term "viable roots" refers to roots that are capable of propagation within the selective rooting medium. Accordingly, viable roots are capable of tissue regeneration and growth within the selective rooting and medium. Plant roots are well known to a person of ordinary skill in the art, and refer to plant parts (including, but not limited to; primary roots, secondary roots, tertiary roots, quaternary roots, lateral roots, root hairs, crown roots, and brace roots) that remain underground or below the surface of a tissue culture medium, and obtain nourishment that is subsequently translocated throughout the plant.

In certain embodiments, the non-germline transformants produce non-viable roots which are brown in color. In other embodiments, the non-germline transformants produce non-viable roots which are black in color. In further embodiments, the non-germline transformants do not produce any root structures.

In this embodiment, the shoots created from soybean germline transformants are identified by detecting whether or not the shoot creates viable roots. As used herein, the term "identified" or "identifying" refers to, determining which plant shoot(s) are created from a soybean germline transformant and selecting these plant shoot(s) from other plant shoot(s) that are created from a soybean non-germline transformant.

The present disclosure can be utilized to identify specific transgenic soybean plants which comprise soybean non-germline transformants, particularly transformants derived from the L1 tissue layer. In particular, the soybean non-germline transformants produced by the disclosed soybean transformation methods are identified early in the transformation process by visually observing the developing roots. In certain embodiments, the non-germline transformants produce non-viable roots which are brown in color. In other embodiments, the non-germline transformants produce non-viable roots which are black in color. In further embodiments, the non-germline transformants do not produce any root structures. The soybean non-germline transformants produced by the disclosed soybean transformation method comprising a transgene integrated within the L1 tissue layer not capable of transmitting the transgene to subsequent generations of soybean plants.

A transformed soybean plant cell, callus, tissue, or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Such selection and screening methodologies are well known to those skilled in the art.

A transgenic soybean plant containing a transgene according to the present disclosure can be produced through selective breeding including, for example, by sexually crossing a first parental plant comprising the molecule, and a second parental plant, thereby producing a plurality of first progeny plants. A first progeny plant may then be selected that is resistant to a selectable marker (e.g., glufosinate, resistance to which may be conferred upon the progeny plant by the heterologous molecule herein). The first progeny plant may then be selfed, thereby producing a plurality of second progeny plants. Then, a second progeny plant may be selected that is resistant to the selectable marker. These steps can further include the back-crossing of the first progeny plant or the second progeny plant to the second parental plant or a third parental plant.

It is also to be understood that two different transgenic soybean plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

A transgene may also be introduced into a predetermined area of the plant genome through homologous recombination. Methods to stably integrate a polynucleotide sequence within a specific chromosomal site of a plant cell via homologous recombination have been described within the art. For instance, site specific integration as described in US Patent Application Publication No. 2009/0111188 A1 involves the use of recombinases or integrases to mediate the introduction of a donor polynucleotide sequence into a chromosomal target. In addition, International Patent Application No. WO 2008/021207, describes zinc finger mediated-homologous recombination to stably integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to stably integrate a polynucleotide sequence into a specific chromosomal site. Finally, the use of meganucleases for targeting donor polynucleotides into a specific chromosomal location was described in Puchta et al., PNAS USA 93 (1996) pp. 5055-5060).

Other various methods for site specific integration within plant cells are generally known and applicable (Kumar et al., Trends in Plant Sci. 6(4) (2001) pp. 155-159). Furthermore, site-specific recombination systems that have been identified in several prokaryotic and lower eukaryotic organisms may be applied for use in plants. Examples of such systems include, but are not limited too; the R/RS recombinase system from the pSR1 plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

In some embodiments disclosed herein, the transforming employs a transformation method elected from the group consisting of *Agrobacterium* transformation, biolistics, calcium phosphate transformation, polybrene transformation, protoplast fusion transformation, electroporation transformation, ultrasonic transformation, liposome transformation, microinjection transformation, naked DNA transformation, plasmid vector transformation, viral vector transformation, silicon carbide mediated transformation, aerosol beaming transformation, or PEG transformation. In some embodiments, the transforming employs an *Agrobacterium* transformation method.

In some embodiments described herein, the population of cells of a soybean plant comprises a soybean plant tissue. In other embodiments, the soybean plant tissue is a L2/L3 tissue layer or a L1 tissue layer. In some embodiments, the L2/L3 tissue layer comprises a germline cell. In some embodiments, the L1 tissue layer comprises a non-germline cell.

In another embodiment, the L2/L3 tissue layer is selected from the group consisting of a meristematic soybean plant tissue, a root soybean plant tissue, and a vascular soybean plant tissue. The meristematic tissue comprises apical meristem, primary meristem, or lateral meristem. These undifferentiated tissues undergo division of new cells which are used for growth or repair of the plant tissues, and are characterized as zones of actively dividing cells. Cell division occurs solely in the meristematic tissues. Apical meristems which are located at the shoot tips are directly involved in shoot elongation. Lateral meristems, such as the vascular meristem, are involved in internal growth. Lateral meristem cells surround the established stem of a plant and cause it to grow laterally. The vascular tissue is a mixture of differentiated cells consisting of parenchyma cells, sclerenchyma cells, fiber cells, and other cells involved in transport (e.g., vessels, tracheids, xylem, or phloem). These types of cells transport fluids, such as water and nutrients, internally within the plant cell.

In yet another embodiment, the L1 tissue layer is selected from the group consisting of a dermal soybean plant tissue, a ground soybean plant tissue, and a mantle soybean plant tissue. The dermal and ground tissue are non-meristematic tissues (i.e., non-dividing tissue) which are made up of parenchyma cells, sclerenchyma cells, and collenchyma cells. The dermal tissue comprises the outermost cell layers of the plants leaves, roots, stems, fruits, or seeds. The ground tissues are simple, non-meristematic tissues made up of parenchyma cells, sclerenchyma cells, chlorenchyma, and collenchyma cells. These cell types generally form the pith and cortex of the stems.

In some embodiments, the meristematic soybean plant tissue comprises one or more of an apical meristem, a primary meristem, or a lateral meristem. In other embodiments, the vascular soybean plant tissue is selected from the group consisting of xylem or phloem. In another embodiment, the dermal soybean plant tissue comprises epidermis. In yet another embodiment, the dermal soybean plant tissue comprises periderm.

In some embodiments, the transgene is contained within at least one gene expression cassette. A widely utilized method for introducing a gene expression cassette comprising a transgene into a plant is based on the natural transformation system of *Agrobacterium* as described previously. In some embodiments, the gene expression cassette comprises a selectable marker gene. In some embodiments, the selectable marker gene is a phosphinothricin acetyl transferase gene. In other embodiments, the gene expression cassette comprises a trait gene. In some embodiments, the gene expression cassette comprises an RNAi gene.

In one embodiment, the selection agent comprises glufosinate. Glufosinate (DL-phosphinothricin) is a non-selective, contact herbicide that controls a broad spectrum of annual and perennial grasses and broadleaf weeds. Glufosinate is a glutamine synthetase inhibitor and irreversibly binds to the glutamate site within glutamine synthetase enzyme. The tolerance to glufosinate, imparted by the pat and dsm-II genes, allows use of an additional mode of action as part of effective herbicide resistance management strategies. Glufosinate herbicides can also be used as selection agents in breeding nurseries to select herbicide-tolerant plants to maintain seed trait purity. Glufosinate may be commercially marketed under the brand names LIBERTY®, BASTA®, and IGNITE®. In some embodiments, the glufosinate concentration within the selective rooting medium is at least 1.0 mg/L. In other embodiments, the glufosinate concentration in the selective rooting medium is from 1.0 mg/L to 10.00 mg/L. In another embodiment, the glufosinate concentration in the selective rooting medium is from 1.0 mg/L to 6.0 mg/L. In yet another embodiment, the glufosinate concentration in the selective rooting medium is 1.0 mg/L.

In one embodiment, the selection agent comprises 2,4-dichlorophenoxyacetic acid (2,4-D). Applications of 2,4-D are primarily used to control broadleaf weeds as most perennial grasses are tolerant to 2,4-D. Most formulations of 2,4-D are applied to foliar portions of a plant and absorbed and translocated throughout the plant tissues. The tolerance to 2,4-D, imparted by the aad-1 and aad-12 genes, allows use of an additional mode of action as part of effective herbicide resistance management strategies. 2,4-D may be commercially marketed under the brand names WEEDAR 64®, BARRAGE®, and FRONTLINE®. In some embodiments, the 2,4-D concentration within the selective rooting medium is at least 2.0 mg/L. In other embodiments, the 2,4-D concentration in the selective rooting medium is from 2.0 mg/L to 120.0 mg/L.

In various embodiments, the selective rooting medium comprises a basal salt, a vitamin, a mineral, and a carbon source. In some embodiments, the basal salt in the rooting media comprises Gamborg's B-5 basal salt (Gamborg, O. L., et al., Nutrient requirements of suspension cultures of soybean root cells. Exp. Cell Res. 50, 151-158 (1968)), Schenk & Hildebrandt basal salt (Schenk, R. U., and Hildebrandt A. C., Medium and techniques for induction and growth of monocotyledonous and dicotyledonous plant cell 50(1): 199-204 (1972)), White's basal salt (White, P. R., The Cultivation of Animal and Plant Cells, 2nd edition, Ronald Press, New York (1963)), Chu (N6) basal salt (Chu, C. C., et al., Establishment of an efficient medium for anther culture of rice, through comparative experiments on the nitrogen sources Scientia Sin. 18, 659-668 (1975)), DKW/ *Juglans* basal salt (Driver, J. A., and Kuniyuki, A. H., In vitro propagation of Paradox walnut *Juglans hindsii×Juglans regia* rootstock. HortScience 19, 507-509), Hoagland's No. 2 basal salt (Hoagland, D. R., and Arnon, D. I., The water-culture method for growing plants without soil Univ. Calif. Coll. Agric. Exp. Sta. Circ. Berkeley, Calif. 347-353 (1938)), Murashige & Skoog basal salt (Murashige, T., and Skoog, F., A revised medium for rapid growth and bioassays with tobacco tissue cultures Physiol. Plant. 15, 473-497 (1962)), and combinations thereof.

In one embodiment, the basal salt is Murashige & Skoog basal salt. In another embodiment, the vitamin is selected from the group consisting of Gamborg's B-5 vitamin, MEM vitamin, Murashige & Skoog vitamin, Schenk & Hildebrandt vitamin, and combinations thereof. In yet another embodiment, the vitamin is Gamborg's B-5 vitamin.

In various embodiments, the carbon source in the rooting media comprises glucose, dextrose, mannose, fructose, galactose, glucuronate, lactose, or glycerol. In a further embodiment, the vitamin used in the liquid media comprises Gamborg's B-5 vitamin (Gamborg, O. L., et al., Nutrient requirements of suspension cultures of soybean root cells. Exp. Cell Res. 50, 151-158 (1968)), MEM vitamin (Sigma-Aldrich, St. Louis, Mo.), Murashige & Skoog vitamin (Murashige, T., and Skoog, F., A revised medium for rapid growth and bioassays with tobacco tissue cultures. Physiol. Plant. 15, 473-497 (1962)), or Schenk & Hildebrandt vitamin (Schenk, R. U., and Hildebrandt A. C., Medium and techniques for induction and growth of monocotyledonous and dicotyledonous plant cell 50(1): 199-204 (1972)). Other embodiments provide for rooting media comprising minerals, antimicrobial compounds, hormones, selection agents, salts, amino acids, a second basal salt, a second carbon source, and/or a second vitamin. Finally, embodiments of the subject disclosure provides for rooting medium in a liquid or solid form. Agar or PHYTAGEL™ (Sigma-Aldrich, St. Louis, Mo.) can be added to the rooting medium to solidify the composition. Various concentrations of agar or PHYTAGEL™ may be incorporated and are known to those with skill in the art. In one embodiment, the carbon source is sucrose.

In certain embodiments, the selective rooting medium is a liquid medium. In other embodiments, the selective rooting medium is a solid medium.

In another embodiment of the present disclosure, a second method of identifying shoots created from soybean germline transformants is provided. The method comprises a) transforming a population of cells of a soybean plant with a transgene, wherein the population of transformed cells comprises transformed germline cells and transformed non-germline cells; b) regenerating shoots from the population of transformed cells; c) isolating the shoots produced by the population of transformed cells; d) subjecting the isolated regenerated shoots to a selective rooting medium, wherein (i) the subjected isolated regenerated shoots produced by the transformed germline cells create viable roots, and (ii) the subjected isolated regenerated shoots produced by the transformed non-germline cells do not create viable roots; and e) identifying the shoots created from soybean germline transformants by detecting whether or not the shoot creates viable roots. The previously described embodiments of the method of identifying shoots created from soybean germline transformants are also applicable to the second method of identifying shoots created from soybean germline transformants described herein.

In yet another embodiment of the present disclosure, a method for identifying a soybean germline transformant is provided. The method comprises a) transforming a population of cells of a soybean plant with a transgene; b) regenerating a shoot from the transformed population of cells of a soybean plant comprising the transgene; c) isolating the regenerated shoot from the transformed population of cells of a soybean plant, wherein the transformed population of cells of a soybean plant comprise the transgene; d) contacting the isolated regenerated shoot with a rooting medium, wherein the rooting medium comprises one or more selection agents; and e) culturing the isolated regenerated shoot on the rooting medium so as to produce viable roots, wherein the production of viable roots identifies the soybean germline transformant. The previously described embodiments of the methods of identifying shoots created from soybean germline transformants are also applicable to the method for identifying a soybean germline transformant described herein.

In another embodiment of the present disclosure, a method of producing a soybean germline transformant or a soybean non-germline transformant is provided. The method comprises the step of culturing one or more regenerated shoots in a rooting medium comprising a selection agent, wherein the one or more regenerated shoots are isolated from a population of soybean cells transformed with a transgene, wherein the one or more regenerated shoots comprising a soybean non-germline transformant does not produce viable roots and the one or more regenerated shoots comprising a soybean germline transformant produces viable roots. The previously described embodiments of the methods of identifying shoots created from soybean germline transformants and the method for identifying a soybean germline transformant are also applicable to the method of producing a soybean germline transformant or a soybean non-germline transformant described herein.

In yet another embodiment of the present disclosure, a method for preventing viable root production from a population of transformed non-germline soybean cells is provided. The method comprises the steps of a) transforming a population of soybean cells with a transgene, wherein the transformed population of soybean cells comprises a population of transformed germline soybean cells and a population of transformed non-germline soybean cells; b) regenerating one or more shoots from the transformed population of soybean cells; c) isolating the one or more regenerated shoots produced from the transformed population of soybean cells; d) contacting the one or more isolated regenerated shoots with a rooting medium, wherein the rooting medium comprises a selection agent; and e) culturing the one or more isolated regenerated shoots on the rooting medium, wherein (i) the one or more isolated regenerated shoots of the transformed germline soybean cells produce viable roots in the presence of the rooting medium comprising a selection agent, and (ii) the one or more isolated regenerated shoots of the transformed non-germline soybean cells prevent viable root production in the presence of the rooting medium comprising a selection agent. The previously described embodiments of the methods of identifying shoots created from soybean germline transformants, the method for identifying a soybean germline transformant, and the method of producing a soybean germline transformant or a soybean non-germline transformant are also applicable to the method for preventing viable root production from a population of transformed non-germline soybean cells described herein.

IV. Agronomic Trait-Encoding Sequences

Some embodiments herein provide a transgene encoding a polypeptide comprising a gene expression cassette. Such a transgene may be useful in any of a wide variety of applications to produce transgenic soybean plants. Particular examples of a transgene comprising a gene expression cassette are provided for illustrative purposes herein and include a gene expression comprising a trait gene, an RNAi gene, or a selectable marker gene.

In engineering a gene for expression in soybean plants, the codon bias of the prospective host plant(s) may be determined, for example, through use of publicly available DNA sequence databases to find information about the codon distribution of plant genomes or the protein coding regions of various plant genes.

In designing coding regions in a nucleic acid for plant expression, the primary ("first choice") codons preferred by the plant should be determined, as well as the second, third, fourth, etc. choices of preferred codons, when multiple choices exist. A new DNA sequence can then be designed which encodes the amino acid sequence of the same peptide, but the new DNA sequence differs from the original DNA sequence by the substitution of plant (first preferred, second preferred, third preferred, or fourth preferred, etc.) codons to specify the amino acid at each position within the amino acid sequence.

The new sequence may then be analyzed for restriction enzyme sites that might have been created by the modifications. The identified sites may be further modified by replacing the codons with first, second, third, or fourth choice preferred codons. Other sites in the sequence that could affect transcription or translation of the gene of interest are stem-loop structures, exon:intron junctions (5' or 3'), poly A addition signals, and RNA polymerase termination signals; these sites may be removed by the substitution of plant codons. The sequence may be further analyzed and modified to reduce the frequency of TA or CG doublets. In addition to the doublets, G or C sequence blocks that have more than about six residues that are the same can affect transcription or translation of the sequence. Therefore, these blocks may be modified by replacing the codons of first or second choice, etc. with the next preferred codon of choice.

Once an optimized (e.g., a plant-optimized) DNA sequence has been designed on paper, or in silico, actual DNA molecules may be synthesized in the laboratory to correspond in sequence precisely to the designed sequence. Such synthetic nucleic acid molecule molecules can be cloned and otherwise manipulated exactly as if they were derived from natural or native sources.

A nucleic acid herein may be cloned into a vector for transformation into prokaryotic or eukaryotic cells for replication and/or expression. Vectors may be prokaryotic vectors; e.g., plasmids, or shuttle vectors, insect vectors, or eukaryotic vectors. A nucleic acid herein may also be cloned into an expression vector, for example, for administration to a plant cell. In certain applications, it may be preferable to have vectors that are functional in *E. coli* (e.g., production of protein for raising antibodies, DNA sequence analysis, construction of inserts, obtaining quantities of nucleic acids).

In an embodiment, a transgene to be expressed is disclosed in the subject application. The gene expression cassette may comprise a selectable marker gene, a trait gene, or an RNAi gene. Examples of a selectable marker gene, a trait gene, and an RNAi gene are further provided below. The methods disclosed in the present application are advantageous in that they provide a method for selecting germline transformants that is not dependent on the specific function of the protein product, or other function, of the transgene.

Transgenes or Coding Sequence that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium falvum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al. (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyubiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 Plant Sci. 89:43) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al. (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).

(R) A developmental-arrestive protein produced in nature by a plant, such as the barley ribosome-inactivating gene that provides an increased resistance to fungal disease (Longemann et al., 1992). Bio/Technology 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

Genes That Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., 1988 EMBO J. 7:1241), which is also known as AHAS enzyme (Miki et al., 1990 Theor. Appl. Genet. 80:449).

(B) One or more additional genes encoding resistance or tolerance to glyphosate imparted by mutant EPSP synthase and aroA genes, or through metabolic inactivation by genes such as GAT (glyphosate acetyltransferase) or GOX (glyphosate oxidase) and other phosphono compounds such as glufosinate (pat and bar genes; DSM-2), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-

SO2CH3-4-CF3 phenyl)propane-1,3-dione and 2-cyano-3-cyclopropyl-1-(2-SO2CH3-4-2,3Cl2-phenyl)propane-1,3-dione, triketones (EP625505, EP625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluoroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., 1992) Proc. Nat. Acad. Sci. USA 89:2624.

(B) Decreased phytate content
  (1) Introduction of a phytase-encoding gene, such as the *Aspergillus niger* phytase gene (Van Hartingsveldt et al., 1993 Gene 127:87), enhances breakdown of phytate, adding more free phosphate to the transformed plant.
  (2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, *Streptococcus* mucus fructosyl-transferase gene (Shiroza et al., 1988) J. Bacteriol. 170:810, *Bacillus subtilis* levansucrase gene (Steinmetz et al., 1985 Mol. Gen. Genel. 200:220), *Bacillus licheniformis* α-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:10450).

To express a selectable marker gene, a trait gene, or an RNAi gene in a soybean cell, a nucleic acid encoding the protein is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* (1990); and *Current Protocols in Molecular Biology* (Ausubel et al., supra.). Bacterial expression systems for expressing a nucleic acid herein are available in, for example, *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The particular expression vector used to transport the genetic information into the cell is selected with regard to the intended use (e.g., expression in plants, animals, bacteria, fungus, and protozoa). Standard bacterial and animal expression vectors are known in the art and are described in detail, for example, U.S. Patent Publication 20050064474A1 and International Patent Publications WO 05/084190, WO05/014791 and WO03/080809. Standard transfection methods can be used to produce bacterial cell lines that express large quantities of protein, which can then be purified using standard techniques.

The selection of a promoter used to direct expression of a nucleic acid herein depends on the particular application. A number of promoters that direct expression of a gene in a plant may be employed in embodiments herein. Such promoters can be selected from constitutive, chemically-regulated, inducible, tissue-specific, and seed-preferred promoters. For example, a strong constitutive promoter suited to the host cell may be used for expression and purification of the expressed proteins. Non-limiting examples of plant promoters include promoter sequences derived from *A. thaliana* ubiquitin-10 (ubi-10) (Callis, et al., 1990, *J. Biol. Chem.*, 265:12486-12493); *A. tumefaciens* mannopine synthase (Δmas) (Petolino et al., U.S. Pat. No. 6,730,824); and/or Cassava Vein Mosaic Virus (CsVMV) (Verdaguer et al., 1996, Plant Molecular Biology 31:1129-1139).

Constitutive promoters include, for example, the core Cauliflower Mosaic Virus 35S promoter (Odell et al. (1985) Nature 313:810-812); Rice Actin promoter (McElroy et al. (1990) Plant Cell 2:163-171); Maize Ubiquitin promoter (U.S. Pat. No. 5,510,474; Christensen et al. (1989) Plant Mol. Biol. 12:619-632 and Christensen et al. (1992) Plant Mol. Biol. 18:675-689); pEMU promoter (Last et al. (1991) Theor. Appl. Genet. 81:581-588); ALS promoter (U.S. Pat. No. 5,659,026); Maize Histone promoter (Chaboute et al. Plant Molecular Biology, 8:179-191 (1987)); and the like.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form, which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically, the protein factor that binds specifically to an inducible regulatory element to activate transcription is present in an inactive form which is then directly or indirectly converted to the active form by the inducer. A plant cell containing an inducible regulatory element may be exposed to an inducer by externally applying the inducer to the cell or plant such as by spraying, watering, heating or similar methods.

Any inducible promoter can be used in embodiments herein. See Ward et al. Plant Mol. Biol. 22: 361-366 (1993). Inducible promoters include, for example and without limitation: ecdysone receptor promoters (U.S. Pat. No. 6,504, 082); promoters from the ACE1 system which respond to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); Tet repressor from Tn10 (Gatz et al., Mol. Gen. Genet. 227: 229-237 (1991); promoters from a steroid hormone gene, the transcriptional activity of which is induced by a glucocorticosteroid hormone, Schena et al., Proc. Natl. Acad. Sci. U.S.A. 88: 10421 (1991) and McNellis et al., (1998) Plant J. 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-1a promoter, which is activated by salicylic acid (see Ono S, Kusama M, Ogura R, Hiratsuka K., "Evaluation of the Use of the Tobacco PR-1a Promoter to Monitor Defense Gene Expression by the Luciferase Bioluminescence Reporter System," Biosci Biotechnol Biochem. 2011 Sep. 23; 75(9):1796-800). Other chemical-regulated promoters of interest include tetracycline-inducible and tetracycline-repressible promoters (see, for example, Gatz et al., (1991) Mol. Gen. Genet. 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; the light-inducible promoter derived from the pea rbcS gene or pea psaDb gene (Yamamoto et al. (1997) Plant J. 12(2):255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6):1129-1138); a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991).

Stress inducible promoters include salt/water stress-inducible promoters such as P5CS (Zang et al. (1997) Plant Sciences 129:81-89); cold-inducible promoters, such as cor15a (Hajela et al. (1990) Plant Physiol. 93:1246-1252), cor15b (Wilhelm et al. (1993) Plant Mol Biol 23:1073-1077), wsc120 (Ouellet et al. (1998) FEBS Lett. 423-324-328), ci7 (Kirch et al. (1997) Plant Mol Biol. 33:897-909), and ci21A (Schneider et al. (1997) Plant Physiol. 113:335-45); drought-inducible promoters, such as Trg-31 (Chaudhary et al (1996) Plant Mol. Biol. 30:1247-57) and rd29 (Kasuga et al. (1999) Nature Biotechnology 18:287-291); osmotic inducible promoters, such as Rab17 (Vilardell et al. (1991) Plant Mol. Biol. 17:985-93) and osmotin (Raghothama et al. (1993) Plant Mol Biol 23:1117-28); heat inducible promoters, such as heat shock proteins (Barros et al. (1992) Plant Mol. 19:665-75; Marrs et al. (1993) Dev. Genet. 14:27-41), smHSP (Waters et al. (1996) J. Experimental Botany 47:325-338); and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al. (1993) Mol. Gen. Genetics 236:331-340). Certain promoters are inducible by wounding, including the Agrobacterium pMAS promoter (Guevara-Garcia et al. (1993) Plant J. 4(3):495-505) and the Agrobacterium ORF13 promoter (Hansen et al., (1997) Mol. Gen. Genet. 254(3):337-343).

Tissue-preferred promoters may be utilized to target enhanced transcription and/or expression within a particular plant tissue. Examples of these types of promoters include seed-preferred expression, such as that provided by the phaseolin promoter (Bustos et al. 1989. *The Plant Cell* Vol. 1, 839-853), and the maize globulin-1 gene, Belanger, et al. 1991 *Genetics* 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al. 1994. T-DNA tagging of a seed coat-specific cryptic promoter in tobacco. Plant J. 4: 567-577), the P-gene promoter from corn (Chopra et al. 1996. Alleles of the maize P gene with distinct tissue specificities encode Myb-homologous proteins with C-terminal replacements. Plant Cell 7:1149-1158, Erratum in Plant Cell. 1997, 1:109), the globulin-1 promoter from corn (Belenger and Kriz. 1991. Molecular basis for Allelic Polymorphism of the maize Globulin-1 gene. Genetics 129: 863-972), and promoters that direct expression to the seed coat or hull of corn kernels, for example the pericarp-specific glutamine synthetase promoter (Muhitch et al., 2002. Isolation of a Promoter Sequence From the Glutamine Synthetase$_{1-2}$ Gene Capable of Conferring Tissue-Specific Gene Expression in Transgenic Maize. Plant Science 163:865-872).

In addition to the promoter, an expression vector typically contains a transcription unit or expression cassette that contains all the additional elements required for the expression of the nucleic acid in host cells, either prokaryotic or eukaryotic. A typical expression cassette thus contains a promoter operably-linked, e.g., to a nucleic acid sequence encoding the protein, and signals required, e.g., for efficient polyadenylation of the transcript, transcriptional termination, ribosome binding sites, or translation termination. Additional elements of the cassette may include, e.g., enhancers and heterologous splicing signals.

Other components of the vector may be included, also depending upon intended use of the gene. Examples include selectable markers, targeting or regulatory sequences, transit peptide sequences such as the optimized transit peptide sequence (see U.S. Pat. No. 5,510,471) stabilizing sequences such as RB7 MAR (see Thompson and Myatt, (1997) *Plant Mol. Biol.,* 34: 687-692 and WO9727207) or leader sequences, introns etc. General descriptions and examples of plant expression vectors and reporter genes can be found in Gruber, et al., "Vectors for Plant Transformation" in *Methods in Plant Molecular Biology and Biotechnology*, Glick et al eds; CRC Press pp. 89-119 (1993).

The selection of an appropriate expression vector will depend upon the host and the method of introducing the expression vector into the host. The expression cassette may include, at the 3' terminus of a heterologous nucleotide sequence of interest, a transcriptional and translational termination region functional in plants. The termination region can be native with the DNA sequence of interest or can be derived from another source. Convenient termination regions are available from the Ti-plasmid of *A. tumefaciens*, such as the octopine synthase and nopaline synthase (nos) termination regions (Depicker et al., Mol. and Appl. Genet. 1:561-573 (1982) and Shaw et al. (1984) Nucleic Acids Research vol. 12, No. 20 pp 7831-7846(nos)); see also Guerineau et al. Mol. Gen. Genet. 262:141-144 (1991); Proudfoot, Cell 64:671-674 (1991); Sanfacon et al. Genes Dev. 5:141-149 (1991); Mogen et al. Plant Cell 2:1261-1272 (1990); Munroe et al. Gene 91:151-158 (1990); Ballas et al. Nucleic Acids Res. 17:7891-7903 (1989); Joshi et al. Nucleic Acid Res. 15:9627-9639 (1987).

An expression cassette may contain a 5' leader sequence. Such leader sequences can act to enhance translation. Translation leaders are known in the art and include by way of example, picornavirus leaders, EMCV leader (Encephalomyocarditis 5' noncoding region), Elroy-Stein et al. Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154:9-20 (1986); human immunoglobulin heavy-chain binding protein (BiP), Macejak et al. Nature 353:90-94 (1991); untranslated leader from the coat protein mRNA of alfalfa mosaic virus (AMV RNA 4), Jobling et al. Nature 325:622-625 (1987); Tobacco mosaic virus leader (TMV), Gallie et al. (1989) Molecular Biology of RNA, pages 237-256; and maize chlorotic mottle virus leader (MCMV) Lommel et al. Virology 81:382-385 (1991). See also Della-Cioppa et al. Plant Physiology 84:965-968 (1987).

The construct may also contain sequences that enhance translation and/or mRNA stability such as introns. An example of one such intron is the first intron of gene II of the histone H3.III variant of *Arabidopsis thaliana*. Chaubet et al. Journal of Molecular Biology, 225:569-574 (1992).

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (see Lebrun et al. U.S. Pat. No. 5,510,417), *Zea mays* Brittle-1 chloroplast transit peptide (Nelson et al. Plant Physiol 117(4):1235-1252 (1998); Sullivan et al. Plant Cell 3(12):1337-48; Sullivan et al., Planta (1995) 196(3):477-84; Sullivan et al., J. Biol. Chem. (1992) 267(26):18999-9004) and the like. In addition, chimeric chloroplast transit peptides are known in the art, such as the Optimized Transit Peptide (see, U.S. Pat. No. 5,510,471). Additional chloroplast transit peptides have been described previously in U.S. Pat. Nos. 5,717,084; 5,728,925. One skilled in the art will readily appreciate the many options available in expressing a product to a particular organelle. For example, the barley alpha amylase sequence is often used to direct expression to the endoplasmic reticulum. Rogers, J. Biol. Chem. 260:3731-3738 (1985).

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, stable integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno or Kozak sequences), modification of nucleic acid molecules to correspond to the codon usage of the host cell, and deletion of sequences that destabilize transcripts.

Reporter or marker genes for selection of transformed cells or tissues or plant parts or plants may be included in the transformation vectors. Examples of selectable markers include those that confer resistance to anti-metabolites such as herbicides or antibiotics, for example, dihydrofolate reductase, which confers resistance to methotrexate (Reiss, Plant Physiol. (Life Sci. Adv.) 13:143-149, 1994; see also Herrera Estrella et al., Nature 303:209-213, 1983; Meijer et al., Plant Mol. Biol. 16:807-820, 1991); neomycin phosphotransferase, which confers resistance to the aminoglycosides neomycin, kanamycin and paromycin (Herrera-Estrella, EMBO J. 2:987-995, 1983 and Fraley et al. Proc. Natl. Acad. Sci USA 80:4803 (1983)); hygromycin phosphotransferase, which confers resistance to hygromycin (Marsh, Gene 32:481-485, 1984; see also Waldron et al., Plant Mol. Biol. 5:103-108, 1985; Zhijian et al., Plant Science 108:219-227, 1995); trpB, which allows cells to utilize indole in place of tryptophan; hisD, which allows cells to utilize histinol in place of histidine (Hartman, Proc. Natl. Acad. Sci., USA 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.); and deaminase from *Aspergillus terreus*, which confers resistance to Blasticidin S (Tamura, Biosci. Biotechnol. Biochem. 59:2336-2338, 1995).

Additional selectable markers include, for example, a mutant acetolactate synthase, which confers imidazolinone or sulfonylurea resistance (Lee et al., EMBO J. 7:1241-1248, 1988), a mutant psbA, which confers resistance to atrazine (Smeda et al., Plant Physiol. 103:911-917, 1993), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., EMBO J. 2:987-992, 1983); streptomycin (Jones et al., Mol. Gen. Genet. 210:86-91, 1987); spectinomycin (Bretagne-Sagnard et al., Transgenic Res. 5:131-137, 1996); bleomycin (Hille et al., Plant Mol. Biol. 7:171-176, 1990);

sulfonamide (Guerineau et al., Plant Mol. Biol. 15:127-136, 1990); bromoxynil (Stalker et al., Science 242:419-423, 1988); glyphosate (Shaw et al., Science 233:478-481, 1986); phosphinothricin (DeBlock et al., EMBO J. 6:2513-2518, 1987), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) *Gene* 70: 25-37); Gordon-Kamm et al., Plant Cell 2:603; 1990; Uchimiya et al., BioTechnology 11:835, 1993; White et al., Nucl. Acids Res. 18:1062, 1990; Spencer et al., Theor. Appl. Genet. 79:625-631, 1990; and Anzai et al., Mol. Gen. Gen. 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); and alkaline phosphatase. In a preferred embodiment, the marker used is beta-carotene or provitamin A (Ye et al, Science 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, The Plant Cell (1990)2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., Plant Cell (1996) δ: 1171-1179; Scheffler et al. Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al, Proc. Natl. Acad. Sci USA (1991) 88:4587-4591; Grotewold et al., Cell (1994) 76:543-553; Sidorenko et al., Plant Mol. Biol. (1999)39:11-19); the bronze locus genes (Ralston et al., Genetics (1988) 119:185-197; Nash et al., Plant Cell (1990) 2(11): 1039-1049), among others.

Further examples of suitable markers include the cyan fluorescent protein (CYP) gene (Bolte et al. (2004) J. Cell Science 117: 943-54 and Kato et al. (2002) Plant Physiol 129: 913-42), the yellow fluorescent protein gene (PHI-YFP™ from Evrogen; see Bolte et al. (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed2 where plant cells transformed with the marker gene are red in color, and thus visually selectable (Dietrich et al. (2002) Biotechniques 2(2):286-293). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech. (1990) 8:241); and a tyrosinase gene (Katz et al., J. Gen. Microbiol. (1983) 129:2703), which encodes an enzyme capable of oxidizing tyrosine to DOPA and dopaquinone, which in turn condenses to form the easily detectable compound melanin. Clearly, many such markers are available and known to one skilled in the art.

V. Assays for Detection of a Transgene or Expressed Product of a Transgene

Various assays can be employed to detect the transgene described in certain embodiments of the disclosure. The following techniques are useful in a variety of situations, and in one embodiment, are useful in detecting the presence of a nucleic acid molecule and/or the polypeptide encoding a transgene in a plant cell. For example, the presence of the molecule can be determined in a variety of ways, including using a primer or probe of the sequence, ELISA assay to detect the encoded protein, a Western blot to detect the protein, or a Northern or Southern blot to detect RNA or DNA. Enzymatic assays for detecting enzyme DGT-14 can be employed. Further, an antibody which can detect the presence of the DGT-14 protein can be generated using art recognized procedures. Additional techniques, such as in situ hybridization, enzyme staining, and immunostaining, also may be used to detect the presence or expression of the recombinant construct in specific plant organs and tissues. The transgene may be selectively expressed in some tissues of the plant or at some developmental stages, or the transgene may be expressed in substantially all plant tissues, substantially along its entire life cycle. However, any combinatorial expression mode is also applicable.

Southern analysis is a commonly used detection method, wherein DNA is cut with restriction endonucleases and fractionated on an agarose gel to separate the DNA by molecular weight and then transferring to nylon membranes. It is then hybridized with the probe fragment which was radioactively labeled with $^{32}P$ (or other probe labels) and washed in an SDS solution.

Likewise, Northern analysis deploys a similar protocol, wherein RNA is cut with restriction endonucleases and fractionated on an agarose gel to separate the RNA by molecular weight and then transferring to nylon membranes. It is then hybridized with the probe fragment which was radioactively labeled with $^{32}P$ (or other probe labels) and washed in an SDS solution. Analysis of the RNA (e.g., mRNA) isolated from the tissues of interest can indicate relative expression levels. Typically, if the mRNA is present or the amount of mRNA has increased, it can be assumed that the corresponding transgene is being expressed. Northern analysis, or other mRNA analytical protocols, can be used to determine expression levels of an introduced transgene or native gene.

In the Western analysis, instead of isolating DNA/RNA, the protein of interest is extracted and placed on an acrylamide gel. The protein is then blotted onto a membrane and contacted with a labeling substance. See e.g., Hood et al., "Commercial Production of Avidin from Transgenic Maize;

Characterization of Transformants, Production, Processing, Extraction and Purification" *Molecular Breeding* 3:291-306 (1997); Towbin et al, (1979) "Electrophoretic transfer of proteins from polyacrylamide gels to nitrocellulose sheets: procedure and some applications" Proc Natl Acad Sci USA 76(9): 4350-4354; Renart et al. "Transfer of proteins from gels to diazobenzyloxymethyl-paper and detection with antisera: a method for studying antibody specificity and antigen structure" Proc Natl Acad Sci USA 76(7): 3116-3120.

The nucleic acid molecule of embodiments of the disclosure, or segments thereof, can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject disclosure. Mutations, insertions, and deletions can be produced in a given primer by methods known to an ordinarily skilled artisan.

Another example of method detection is the pyro sequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension. (This technique is used for initial sequencing, not for detection of a specific gene when it is known.)

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

Embodiments of the subject disclosure are further exemplified in the following Examples. It should be understood that these Examples are given by way of illustration only. From the above embodiments and the following Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1: Soybean Growth Response to Varying Concentrations of Glufosinate

Growth response studies to varying concentrations of selection agent were conducted using non-transgenic soybean shoots. In this example, glufosinate was used as the exemplary selection agent. Soybean shoots were regenerated from split-seed soybean tissues and cultivated on Shoot Induction medium until shoots had developed and were ready for transfer to rooting medium. Several different concentrations of glufosinate (0, 0.25 mg/L, 0.50 mg/L, 1 mg/L, 2 mg/L, 3 mg/L, 4 mg/L, 5 mg/L, and 6 mg/L) were incorporated into rooting medium (MS salts, B5 vitamins, 28 mg/L ferrous, 38 mg/L $Na^2EDTA$, 20 g/L sucrose and 0.59 g/L MES, 50 mg/L asparagine, 100 mg/L L-pyroglutamic acid, and 7 g/L NOBLE™ agar, pH 5.6) to determine which concentrations of glufosinate inhibited root development. While 100% of the soybean shoots produced roots when cultivated in rooting media without glufosinate, no root formation was observed for soybean shoots cultivated in rooting media supplemented with 1 to 6 mg/L glufosinate. However, 90% and 50% of the soybean shoots cultivated in rooting medium containing glufosinate at concentrations of 0.25 mg/L and 0.5 mg/L, respectively, produced roots. (see Table 1). The effective glufosinate concentration for inhibition of soybean shoot growth and development was determined to be at least 1.0 mg/L of glufosinate. Higher concentrations of glufosinate (e.g., concentrations greater than 1.0 mg/L) were effective in inhibiting root development.

TABLE 1

Effects of different concentrations of glufosinate
on rooting of soybean shoots regenerated in vitro.

| Glufosinate Concentration | Number of Shoots Cultivated | Number of Shoots Producing Roots | Percentage of Shoots that Produced Roots |
|---|---|---|---|
| 0 mg/L | 30 | 30 | 100% |
| 0.25 mg/L | 10 | 9 | 90% |
| 0.5 mg/L | 10 | 5 | 50% |
| 1.0 mg/L | 30 | 0 | 0% |
| 2.0 mg/L | 30 | 0 | 0% |
| 3.0 mg/L | 30 | 0 | 0% |
| 4.0 mg/L | 25 | 0 | 0% |
| 5.0 mg/L | 25 | 0 | 0% |
| 6.0 mg/L | 25 | 0 | 0% |

Example 2: DNA Construct

A single binary vector labeled as pDAB9381 (FIG. 1) was constructed using art recognized procedures. see Sambrook et al. (1989) and Ausubel et al. (1997). pDAB9381 contains two Plant Transcription Units (PTUs). The first PTU (SEQ ID NO:1) consists of the *Arabidopsis thaliana* ubiquitin-10 promoter (AtUbi10 promoter; Callis J, et al., (1990) *J. Biol. Chem.* 265:12486-12493) which drives the yellow fluorescence protein coding sequence (PhiYFP; Shagin, et al., (2004) *Mol. Biol. Evol.* 21(5), 841-850) that contains an intron isolated from the *Solanum tuberosum*, light specific tissue inducible LS-1 gene (ST-LS 1 intron; Genbank Acc No. X04753), and is terminated by the *Agrobacterium tumefaciens* open reading frame-23 3' untranslated region (AtuORF23 3'UTR; EP Patent No. 222493). The second PTU (SEQ ID NO:2) was cloned within the isopentenyl-transferase coding sequence (ipt CDS; Genbank Acc No. X00639.1), consisting of the Cassava Vein Mosaic Virus promoter (CsVMV promoter; Verdaguer B, et al., (1996) *Plant. Mol. Biol.* 31:1129-1139) which is used to drive the phosphinothricin acetyl transferase coding sequence (PAT; Wohlleben W, et al., (1988) Gene 70:25-38), terminated by the *A. tumefaciens* open reading frame-1 3' untranslated region (AtuORF1 3'UTR; Huang M L et al., (1990) *J. Bacteriol.*, 172:1814-1822). The resulting binary vector contained a visual reporter gene and an antibiotic selectable marker gene and was subsequently used for the transformation of soybean. *Agrobacterium tumefaciens* strain EHA105 (Hood E., Helmer G., Fraley R., Chilton M., (1986) *J. Bacteriol.*, 168: 1291-1301) was electroporated with the binary vector pDAB9381. Isolated colonies were identified which grew up on YEP media containing the antibiotic spectinomycin. Single colonies were isolated and the presence of the pDAB9381 binary vector was confirmed via restriction enzyme digestion.

Example 3: Preparation of Plant Material

Mature seeds of soybean (*Glycine max* cv. Maverick) were surface-sterilized using chlorine gas in a large PYREX™ desiccator for about 16 hours. Following sterilization, the seeds were placed in a laminar flow hood for about 30 minutes to remove the excess chlorine gas. Sterilized seeds were soaked in sterile water in PETRI™ dishes for about 16 hours at 24° C. The PETRI™ dishes were placed in black boxes to keep the soybeans seeds in the dark.

Example 4: Plant Transformation

Cotyledonary Node Soybean Transformation
*Agrobacterium*-mediated transformation of soybean (*Glycine max* c.v., Maverick) was performed using an *Agrobacterium*-strain harboring a binary vector via a modified procedure of Zeng P., et al., (2004), *Plant Cell Rep.*, 22(7): 478-482. In this example, glufosinate was used as the exemplary selection agent. The protocol was modified to include the herbicide glufosinate as a selective agent. In addition, another modification included the germination of sterilized soybean seeds on B5 basal medium (Gamborg et al., (1968) *Exp Cell Res*. April; 50(1):151-8.) solidified with 3 g/L PHYTAGEL™ (Sigma-Aldrich, St. Louis, Mo.). The final modification to the protocol deploys the use of cotyledonary node explants prepared from 5-6 days old seedlings and infected with *Agrobacterium* as described by Zhang et al., (1999) *Plant Cell Tiss. Org.* 56: 37-46. As described in Zeng et al., (2004), co-cultivation is carried out for 5 days on the co-cultivation medium. Shoot initiation, shoot elongation, and rooting media are supplemented with 50 mg/L CEFOTAXIME™, 50 mg/L TIMENTIN™, 50 mg/L VANCOMYCIN™, and solidified with 3 g/L PHYTAGEL™.

Half Seed Soybean Transformation Method
*Agrobacterium*-mediated transformation of soybean (*Glycine max* c.v., Maverick) was performed using an *Agrobacterium*-strain harboring a binary vector via a modified procedure Paz M., et al., (2005) *Plant Cell Rep.*, 25: 206-213. Briefly, soybean seeds were cut in half by a longitudinal cut along the hilum to separate the seed and remove the seed coat. The embryonic axis was excised and any axial shoots/buds were removed from the cotyledonary node. The resulting half seed explants were infected with *Agrobacterium*. Shoot initiation, shoot elongation, and rooting media were supplemented with 50 mg/L CEFOTAXIME™, 50 mg/L TIMENTIN™, 50 mg/L VANCOMYCIN™, and solidified with 3 g/L PHYTAGEL™. Glufosinate selection was employed to inhibit the growth of non-transformed shoots.

Split Seed with Partial Embryo Axis Soybean Transformation Method
*Agrobacterium*-mediated transformation of soybean (*Glycine max* c.v., Maverick) was performed using an *Agrobacterium*-strain harboring the pDAB9381 binary vector via the split-seed explant with partial embryo axis soybean transformation protocol described in U.S. Filing No. 61/739,349, herein incorporated by reference. After transformation, the soybean tissues were cultured using the tissue culture methods described below.

Example 5: Tissue Culture

The transformed soybean seeds were cultivated using the tissue culture protocol as described in U.S. Filing No. 61/739,349, herein incorporated by reference. Co-cultivation of the soybean plant seeds with an *Agrobacterium* strain containing the pDAB9381 plasmid was carried out for 5 days on co-cultivation medium covered with a filter paper. After 5 days of incubation on the co-cultivation medium, the explants were washed in liquid Shoot Induction (SI) medium for about 5 to 10 minutes. The explants were then cultured onto Shoot Induction-I (SI-I) medium. The soybean seeds were oriented so the flat side of the soybean seed faced up and the nodal end of the soybean cotyledon was imbedded into the SI-I medium. After 2 weeks of culture at 24° C. with an 18 hour photoperiod, the explants were transferred to the Shoot Induction-II (SI-II) medium supplemented with 6 mg/L glufosinate. After 2 weeks on SI-II medium, the cotyledons were removed from the explants, a flush shoot pad was excised by making a cut at the base of the cotyledon, and the isolated shoot was transferred to the Shoot Elongation (SE) medium. The cultures were transferred to fresh SE medium every two weeks. PETRI™ dishes were not wrapped with filter paper throughout the shoot induction and shoot elongation stages. Lighting sources were provided with an illumination of 80-90 μmoles s-1m-2 for the transformed tissues during shoot induction and shoot elongation.

The elongated shoots were dipped in 1 mg/L indole 3-butyric acid (IBA) for about 1 to 3 minutes to promote rooting prior to transferring of the isolated shoots to rooting medium (MS salts, B5 vitamins, 28 mg/L ferrous, 38 mg/L Na$^2$EDTA, 20 g/L sucrose and 0.59 g/L MES, 50 mg/L asparagine, 100 mg/L L-pyroglutamic acid, and 7 g/L NOBLE™ agar, pH 5.6) in phyta trays. A selection agent of glufosinate at a concentration of 1 mg/L was incorporated into the rooting medium for a subset of the transformation experiments.

Following culturing in the rooting medium at 24° C., with an 18 hour photoperiod, for 1-2 weeks, the soybean shoots that produced healthy, viable roots were transferred to soil. The soybean shoots comprising healthy, viable roots were placed in soil which was contained in an open plastic sundae cup. The plastic sundae cups containing the transferred soybean shoots comprising roots were placed in a CONVIRON™ for acclimatization of soybean plantlets. The rooted soybean plantlets were acclimated in the open sundae cups for several weeks before the plantlets were transferred to the greenhouse.

Example 6: Use of Selection Agents in Rooting Medium

Incorporation of a section agent comprising glufosinate in soybean tissue culture rooting medium was tested to reduce the formation of non-germline, chimeric soybean transformation events and escapes. Following *Agrobacterium*-mediated transformation of soybean (cv. Maverick) with the binary vector, pDAB9381, soybean shoots were regenerated and cultured onto rooting medium that contained a selection agent comprising glufosinate. After root development was initiated on the rooting media comprising glufosinate, the roots were tested for transgene expression (yellow fluorescence protein). Presence of an actively expressing transgene within the developed roots indicated that the $L_2/L_3$ tissue layers were transformed, thereby resulting in soybean germline transformants.

Figure 2:
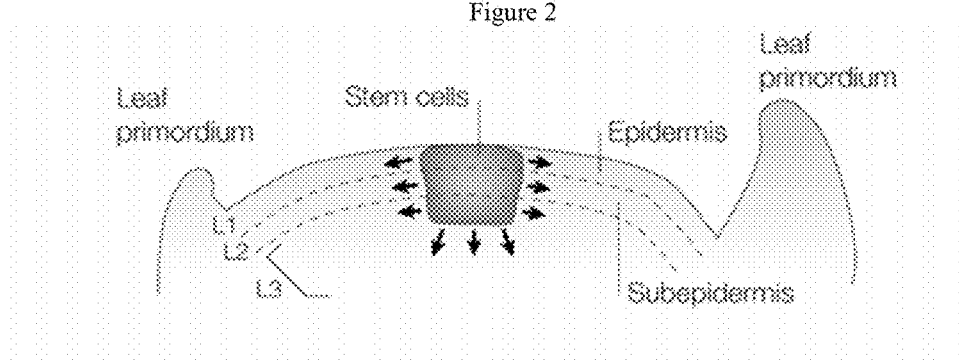
FIG. 2 illustrates a median vertical section of a soybean shoot apical meristem as described in Clark S., (2001) Nature Reviews; Molecular Cell Biology 2; 276-284.
Figure 3:
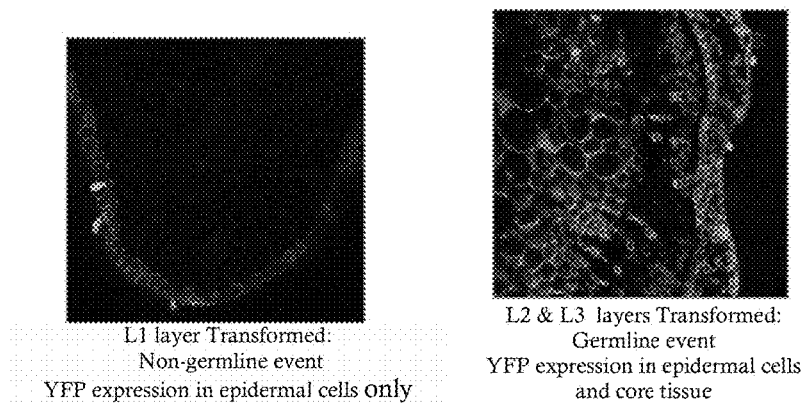
FIG. 3 illustrates a cross section of the soybean stem showing yellow fluorescence protein transgene expression in soybean tissue layers. Expression of the yellow fluorescence protein transgene within the L1 soybean tissue layer indicates non germline transformants and the L2/L3 soybean tissue layers indicate germline transformants. The L1 tissue layer transformants produce the Yellow Flourescent Protein in only the epidermal cell layer as observed using confocal microscopy. The L2/L3 tissue layer transformants produce the Yellow Flourescent Protein in the epidermal and core cells as observed using confocal microscopy.
Figure 5:
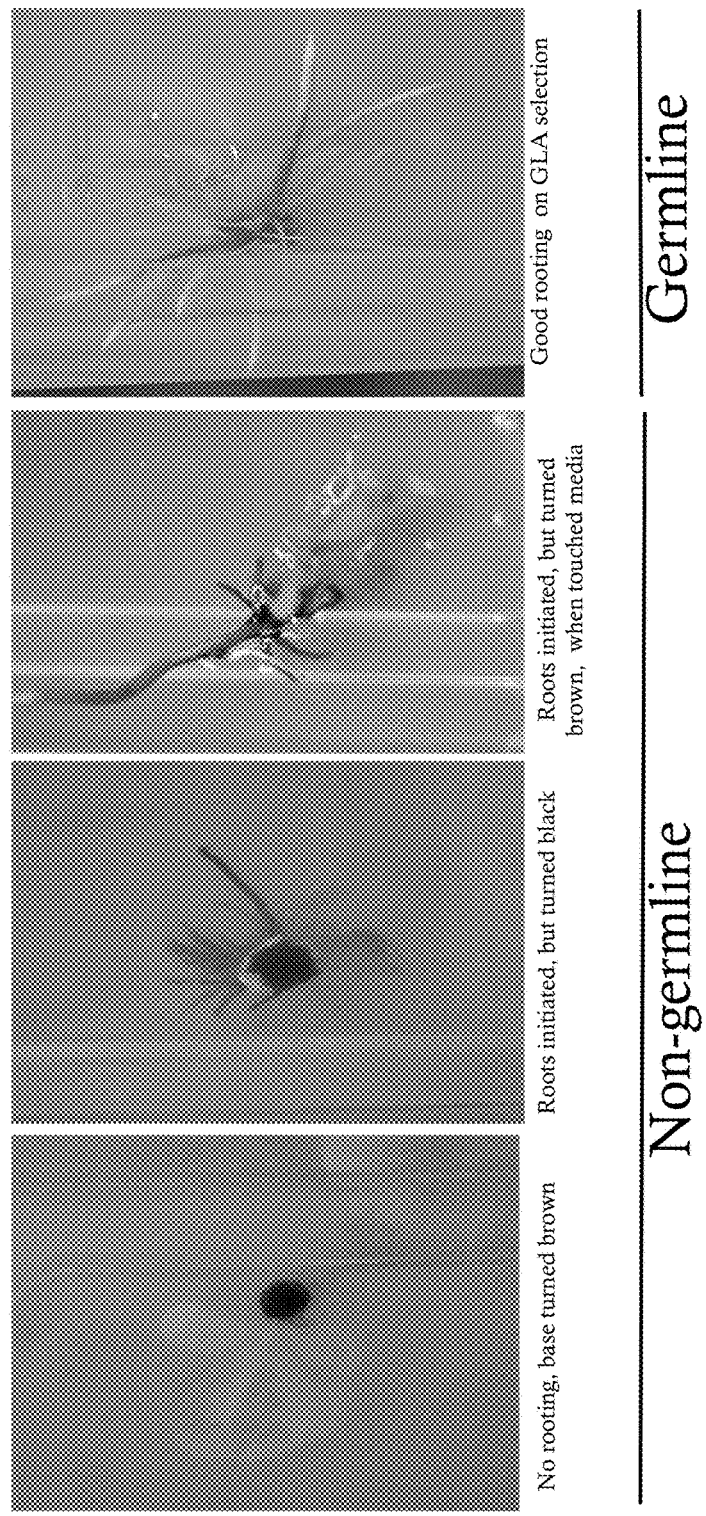
FIG. 5 illustrates the phenotype of soybean plants cultured in rooting medium comprising 1 mg/L of glufosinate. The non-germline transformants resulted in three phenotypes: (1) no roots were produced; (2) roots were produced and turned brown; and, (3) roots were produced and turned black. Comparatively, the gemline transformants resulted in a phenotype in which healthy viable roots were produced.

A total of 531 transgenic soybean shoots were produced using the transformation method described above and transferred onto rooting medium containing the selection agent glufosinate. The shoots were observed for root development and shoots which produced viable, white roots were further assayed for expression of the yellow fluorescence protein transgene via microscopy. (see Table 2). A correlation was observed between yellow fluorescence protein transgene expression and viable, white root formation, wherein a significant majority of the viable, white roots expressed the yellow fluorescence protein transgene in root tissues. (see FIG. 2, FIG. 3, and FIG. 5). Microscopy results confirmed that about 92% of the soybean plants produced from rooting medium comprising a selection agent were transgenic as these soybean plants expressed the yellow fluorescence protein transgene. (see FIG. 2, FIG. 3, and FIG. 5).

These results were comparable to the results observed in soybean shoots cultured on rooting medium that did not contain a selection agent. The control conditions in which no selection agent was included in the rooting medium resulted in soybean shoots that produced healthy roots. However, only 51% of the rooted plants expressed the yellow fluorescence protein transgene in root tissues. (see FIG. 5 and Table 2).

Conversely, when the non-germline or chimeric transformed shoots were transferred to rooting medium comprising a selection agent, either the shoots did not develop roots or the few roots that did develop turned brown or black. The shoots that produced brown or black roots did not express the yellow fluorescence protein transgene in root tissues, thereby indicating that the germline tissues were not transformed with the yellow fluorescence protein transgene. These results indicated that non-germline soybean transformation events either do not form roots or develop brown/black roots when cultured in rooting medium comprising a selection agent (e.g., glufosinate). The non-germline transformed soybean shoots either do not survive or can be distinguished visually (e.g., identified by the production of brown/black roots) and can be culled at the rooting medium selection stage of tissue culture (see FIG. 5).

TABLE 2

Presence or absence of yellow fluorescence protein transgene expression in root tissues of regenerated soybean plantlets cultured in rooting medium with and without the selection agent, glufosinate.

| Selection at Rooting Stage | Number of Plants Rooted | Number of Plants with Viable, White Roots (%) | Number of Plants with Unhealthy, Brown/Black Roots (%) | Number of Plants with YFP Expression (%) | Number of Plants with no YFP Expression (%) |
| --- | --- | --- | --- | --- | --- |
| Without Selection (Control) | 258 | 258 (100%) | 0 (0%) | 132 (51%) | 126 (49%) |
| With Selection of Glufosinate (1 mg/L) | 531 | 319 (60%) | 212 (40%) | 271 (51%) | 260 (49%) |

Example 7: Heritability of Transgenic Soybean Events Produced on Rooting Medium Comprising a Selection Agent A total of 153 transgenic soybean events were isolated and grown to maturity. These soybean events were self-fertilized to produce seed that was obtained and analyzed for heritability. All of the 153 transgenic soybean events were confirmed to contain the yellow fluorescent protein and phosphinothricin acetyltransferase transgenes via molecular analysis in the parental $T_0$ soybean plants. For each of the 153 transgenic soybean events, 15 seeds were obtained and germinated in soil under conventional green house conditions. The transgenic soybean plants were grown to the V1 stage of development and were sprayed with 411 g ae/ha glufosinate, which was used as the exemplary selection agent in this example. After treatment with glufosinate, the soybean plants were observed and graded as resistant or susceptible to glufosinate. The transgenic soybean events that produced at least one $T_1$ seedling were determined to be a heritable event.

Of 153 transgenic soybean events analyzed, 48% of the events produced at least one soybean seed that was resistant to glufosinate and was determined to be a heritable event. Of the tested $T_1$ transgenic soybean events, 76 of the 153 transgenic soybean events were produced from soybean shoots that developed brown/black roots when transferred to a rooting medium comprising glufosinate. A total of 93% of these transgenic soybean events produced soybean plants that were susceptible to the application of glufosinate and were determined to be non-heritable events. (see Table 3). Of the tested $T_1$ transgenic soybean events, 77 of the 153 transgenic soybean events were produced from soybean shoots that developed healthy, white roots when transferred to rooting medium comprising glufosinate. A total of 90% of these transgenic soybean events produced soybean plants that were resistant to the application of glufosinate and were determined to be heritable events. (see Table 3). Thus, by employing glufosinate selection within the rooting medium stage of tissue culture, and advancing the germline transformed soybean events comprising healthy, white roots, the frequency of heritable soybean events increases from 48% to 90%. Conversely, about 93% of the non-germline transformed events can be identified and culled at the rooting stage of transformation by identifying and eliminating soybean transformants comprising brown/black roots. (see Table 3).

TABLE 3

Heritability analysis of transgenic soybean events produced on rooting medium comprising glufosinate selection.

|   | Number of $T_1$ transgenic soybean events analyzed | Percentage of heritable events | Percentage of non-heritable events |
| --- | --- | --- | --- |
| Total | 153 | 48% | 52% |
| Brown/Black Roots | 76 | 7% | 93% |
| White Roots | 77 | 90% | 10% |

Figure 4:
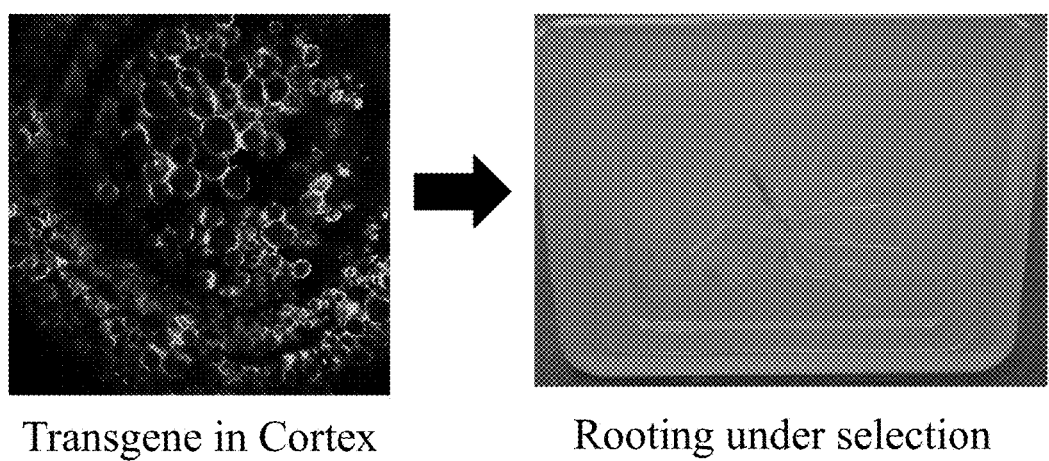
FIG. 4 illustrates the expression of Yellow Fluorescent Protein in cortex cells that comprise the L2/L3 tissue layers and the subsequent development of root structures in rooting medium comprising 1 mg/L of glufosinate.

As shown in Table 4, specific $T_1$ soybean events that were heritable and were confirmed via molecular confirmation analysis to possess a copy of the yellow fluorescent protein transgene were derived from $T_0$ soybean plants that were cultured in rooting medium comprising a selection agent and were confirmed via microscopy to express the yellow fluorescent protein transgene. The results of the studies indicate that there is a correlation between the yellow fluorescent protein transgene expression in roots of $T_0$ plants and the heritablity of the yellow fluorescent protein transgene to $T_1$ plants. Considering that the soybean roots are developed from germline tissues (see FIG. 3 and FIG. 4), incorporation of a selection agent within rooting medium selects for the development of soybean germline transformants, and can be used to cull the soybean non-germline transformants.

TABLE 4

Correlation between yellow fluorescent protein transgene expression in roots of $T_0$ plants and molecular confirmation of the yellow fluorescent protein transgene in $T_1$ soybean progeny plants.

| Transgenic Event Number | $T_0$ YFP Expression in Roots | $T_1$ Molecular Confirmation of YFP in Plant Tissue |
| --- | --- | --- |
| [206]-2604 | Yes | Yes |
| [206]-2605 | Yes | Yes |

TABLE 4-continued

Correlation between yellow fluorescent protein transgene expression in roots of $T_0$ plants and molecular confirmation of the yellow fluorescent protein transgene in $T_1$ soybean progeny plants.

| Transgenic Event Number | $T_0$ YFP Expression in Roots | $T_1$ Molecular Confirmation of YFP in Plant Tissue |
| --- | --- | --- |
| [208]-2651 | Yes | Yes |
| [209]-2658 | Yes | Yes |

Figure 6:
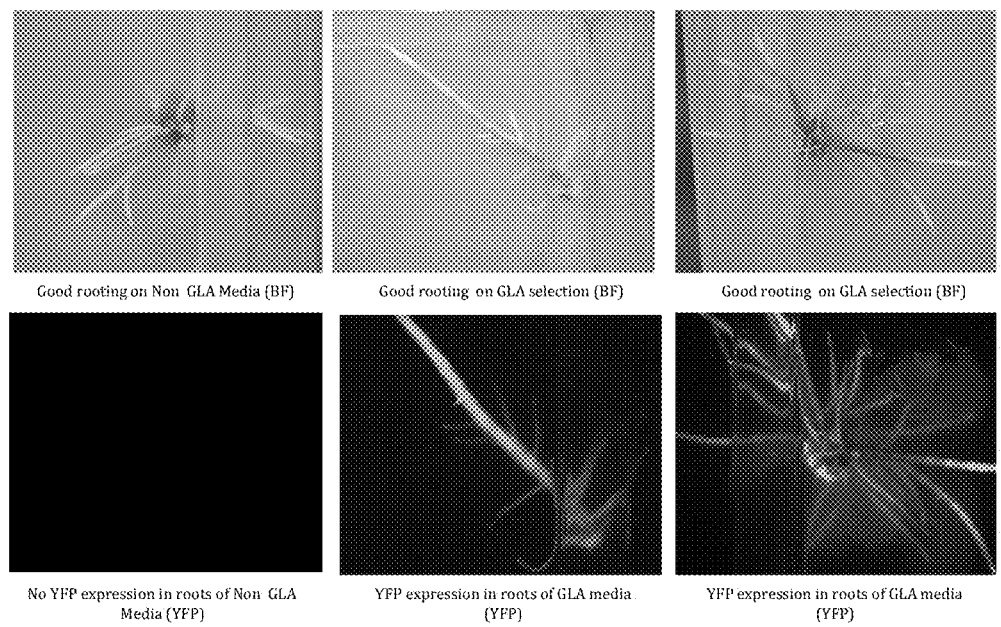
FIG. 6 illustrates the expression of Yellow Fluorescent Protein in roots that were developed in rooting mediums with and without glufosinate selection.
Figure 7A:
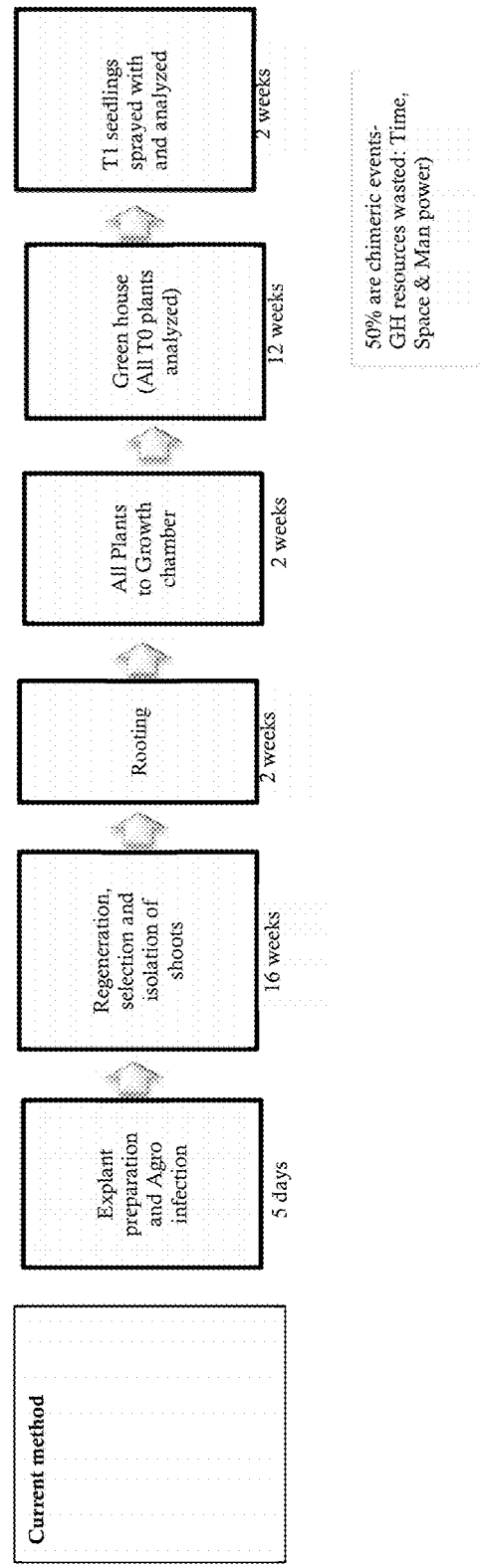
FIGS. 7A-7B illustrate the soybean transformation process and compares the disclosed method to currently used methods for transformation of soybeans.
Figure 7B:
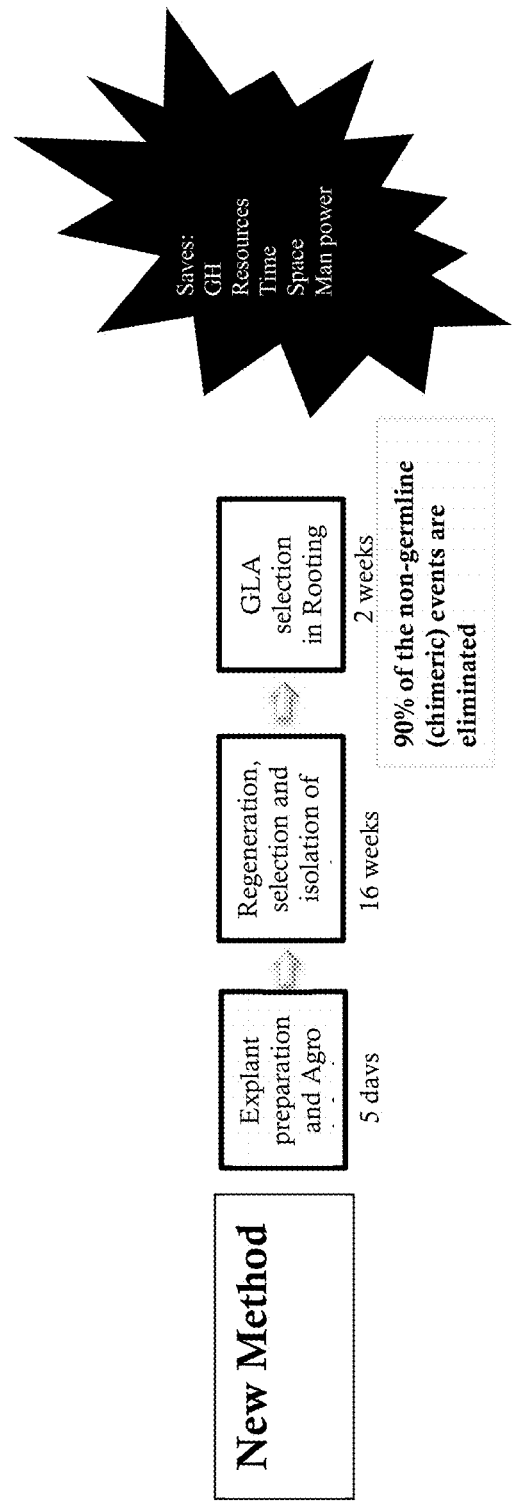

Example 8: Detection and Elimination of Non-Germline Soybean Transformation Events A novel and efficient method is disclosed for elimination of non-germline or chimeric soybean transformants at an early stage in the soybean transformation process. The methodology deploys the incorporation of a selection agent in rooting medium for selection of germline soybean transformants. In this example, glufosinate at 1 mg/L was used as the exemplary selection agent. When the regenerated soybean shoots are cultured on rooting medium comprising glufosinate, the non-germline or chimeric soybean transformation events do not produce viable roots. The non-germline or chimeric soybean transformation events produce unhealthy, brown/black roots or they do not produce any roots. As such, the non-germline or chimeric soybean transformation events can be distinguished visually and culled at an early stage in the soybean transformation process. Comparatively, the germline soybean transformation events produce healthy, viable roots in the presence of glufosinate and the rooted plantlets and can be identified and selected for advancement to the greenhouse for $T_1$ seed production. Glufosinate was evaluated as the selection agent in the rooting medium for selection of the germline soybean transformants. Use of glufosinate as a selection agent at a concentration of at least 1 mg/L selection was found to be effective for eliminating about 93% of the non-germline (chimeric) events based on root phenotype (brown/black roots or no root development). Comparatively, the use of glufosinate as a selection agent at a concentration of at least 1 mg/L selection was effective for identifying germline soybean transformation events, about 90% of advanced soybean transformation events that produced viable, healthy roots in soybean medium comprising a selection agent were confirmed to be germline soybean transformants. (FIG. 6).

Example 9: Detection and Elimination of Non-Germline Soybean Transformation Events Through the Use of a Glyphosate Selection Agent Binary vectors comprising the dgt-28 transgene can be constructed using art recognized procedures. The dgt-28 transgene can provide robust tolerance to the application of commercial concentrations of glyphosate. Exemplary binary vectors comprising the dgt-28 transgene are further described in U.S. patent Ser. No. 13/757,536, herein incorporated by reference. A binary vector containing the dgt-28 antibiotic selectable marker gene can subsequently be used for the transformation of soybean. A strain of *Agrobacterium tumefaciens* strain can be electroporated with the binary vector comprising a dgt-28 antibiotic selectable marker gene. Single colonies are isolated and the presence of the binary vector can be confirmed via restriction enzyme digestion.

Plant transformation can be carried out using any known soybean transformation protocol. Exemplary soybean transformation methods include the modified cotyledonary node soybean transformation procedure of Zeng P. (2004), the modified half seed soybean transformation of Paz M. (2005), or the split seed with partial embryo axis soybean transformation method of U.S. Filing No. 61/739,349. After transformation the soybean tissues are cultured using the tissue culture methods described below.

Transformed soybean seed are cultivated using a modified tissue culture protocol as described in U.S. Filing No. 61/739,349, herein incorporated by reference, wherein the selective agent is glyphosate. Co-cultivation of the soybean plant seeds with *Agrobacterium* can be carried out for 5 days on co-cultivation medium covered with a filter paper. After 5 days of incubation on the co-cultivation medium, the explants can be washed in liquid Shoot Induction (SI) medium for about 5 to 10 minutes. The explants can then be cultured onto Shoot Induction-I (SI-I) medium. The soybean seeds can be oriented so the flat side of the soybean seed faced up and the nodal end of the soybean cotyledon is imbedded into the SI-I medium. After 2 weeks of culture at 24° C. with an 18 hour photoperiod, the explants can be transferred to the Shoot Induction-II (SI-II) medium supplemented with 0.01 mM to 1.0 mM glyphosate. After 2 weeks on SI-II medium, the cotyledons can be removed from the explants, a flush shoot pad can be excised by making a cut at the base of the cotyledon, and the isolated shoot can be transferred to the Shoot Elongation (SE) medium. The cultures can be transferred to fresh SE medium every two weeks. PETRI™ dishes may not be wrapped with filter paper throughout the shoot induction and shoot elongation stages. Lighting sources can be provided with an illumination of 80-90 µmoles s-1m-2 for the transformed tissues during shoot induction and shoot elongation.

The elongated shoots can be dipped in 1 mg/L indole 3-butyric acid (IBA) for about 1 to 3 minutes to promote rooting prior to transferring of the isolated shoots to rooting medium (MS salts, B5 vitamins, 28 mg/L ferrous, 38 mg/L Na$^2$EDTA, 20 g/L sucrose and 0.59 g/L MES, 50 mg/L asparagine, 100 mg/L L-pyroglutamic acid, and 7 g/L NOBLE™ agar, pH 5.6) in phyta trays. A selection agent of glyphosate at a concentration of 0.01 mM to 1.0 mM can be incorporated into the rooting medium for a subset of the transformation experiments.

Following culturing in the rooting medium at 24° C., with an 18 hour photoperiod, for 1 to 2 weeks, the soybean shoots which produced healthy, viable roots can be transferred to soil. The soybean shoots comprising healthy, viable roots can be placed in soil which is contained in an open plastic sundae cup. The plastic sundae cups containing the transferred soybean shoots comprising roots can be placed in a CONVIRON™ for acclimatization of soybean plantlets. The rooted soybean plantlets can be acclimated in the open sundae cups for several weeks before the plantlets are transferred to the greenhouse.

Incorporation of a section agent comprising glyphosate in soybean tissue culture rooting medium can be tested to eliminate non-germline, chimeric soybean transformation events and escapes. Following *Agrobacterium*-mediated transformation of soybean (cv. Maverick) with a binary vector containing the dgt-28 transgene, soybean shoots can be regenerated and cultured onto rooting medium that contains a selection agent comprising glyphosate. The shoots can be observed for root development and shoots which produce viable, white roots can be further assayed for expression of transgene via microscopy. The roots can be further tested via molecular confirmation for presence of the transgene. Presence of an actively expressing transgene within developed roots may be indicative that the $L_2/L_3$ tissue layers are transformed, thereby resulting in soybean germline transformants. A correlation may be observed between transgene expression and viable, white root formation, wherein a significant majority of the viable, white roots may express the transgene in root tissues.

These results may be comparable to soybean shoots cultured on rooting medium that does not contain a selection agent. The control conditions in which no selection agent is included in the rooting medium may result in soybean shoots that produce healthy roots. However, only about 50% of the rooted plants may express the transgene in root tissues.

Conversely, when the non-germline or chimeric transformed shoots are transferred to rooting medium comprising a selection agent, the shoots may not develop roots or the few roots that develop may turn brown or black. The shoots that produce brown or black roots may not express the transgene in root tissues, thereby indicating that the germline tissues may not be transformed with the transgene. These results may indicate that non-germline soybean transformation events either do not form roots or develop brown/black roots when cultured in rooting medium comprising a selection agent. The non-germline transformed soybean shoots may not survive or maybe distinguished visually, as identified by the production of brown/black roots, and thus may be culled at the rooting medium selection stage of tissue culture.

Example 10: Detection and Elimination of Non-Germline Soybean Transformation Events Through the Use of a 2,4-D Selection Agent Binary vectors comprising the aad-12 transgene can be constructed using art recognized procedures. The aad-12 transgene provides robust tolerance to the application of commercial concentrations of 2,4-D. Exemplary binary vectors comprising the aad-12 transgene are further described in U.S. Pat. No. 8,283,522 herein incorporated by reference. A binary vector containing the aad-12 antibiotic selectable marker gene may subsequently be used for the transformation of soybean. A strain of *Agrobacterium tumefaciens* strain may be electroporated with the binary vector comprising a aad-12 antibiotic selectable marker gene. Single colonies can be isolated and the presence of the binary vector is confirmed via restriction enzyme digestion.

Plant transformation can be carried out using any known soybean transformation protocol. Exemplary soybean transformation methods include the modified cotyledonary node soybean transformation procedure of Zeng P. (2004), the modified half seed soybean transformation of Paz M. (2005), or the split seed with partial embryo axis soybean transformation method of U.S. Filing No. 61/739,349. After transformation, the soybean tissues can be cultured using the tissue culture methods described below.

Transformed soybean seed can be cultivated using a modified tissue culture protocol as described in U.S. Filing No. 61/739,349, herein incorporated by reference, wherein the selective agent is 2,4-D. Co-cultivation of the soybean plant seeds with *Agrobacterium*, can be carried out for 5 days on co-cultivation medium covered with a filter paper. After 5 days of incubation on the co-cultivation medium, the explants can be washed in liquid Shoot Induction (SI) medium for about 5 to 10 minutes. The explants can then be cultured onto Shoot Induction-I (SI-I) medium. The soybean seeds are oriented so the flat side of the soybean seed face up and the nodal end of the soybean cotyledon is imbedded into the SI-I medium. After 2 weeks of culture at 24° C. with an 18 hour photoperiod, the explants can be transferred to the Shoot Induction-II (SI-II) medium supplemented with 2 to 120 mg/L 2,4-D. After 2 weeks on SI-II medium, the cotyledons can be removed from the explants, wherein a flush shoot pad is excised by making a cut at the base of the cotyledon, and the isolated shoot is transferred to the Shoot Elongation (SE) medium. The cultures can be transferred to fresh SE medium every two weeks. PETRI™ dishes may not be wrapped with filter paper throughout the shoot induction and shoot elongation stages. Lighting sources can be provided with an illumination of 80-90 µmoles s-1m-2 for the transformed tissues during shoot induction and shoot elongation.

The elongated shoots can be dipped in 1 mg/L indole 3-butyric acid (IBA) for about 1 to 3 minutes to promote rooting prior to transferring of the isolated shoots to rooting medium (MS salts, B5 vitamins, 28 mg/L ferrous, 38 mg/L Na²EDTA, 20 g/L sucrose and 0.59 g/L MES, 50 mg/L asparagine, 100 mg/L L-pyroglutamic acid, and 7 g/L NOBLE™ agar, pH 5.6) in phyta trays. A selection agent of 2,4-D, at a concentration of about 2 to 120 mg/L, is incorporated into the rooting medium for a subset of the transformation experiments.

Following culturing in the rooting medium at 24° C., 18 hour photoperiod, for 1-2 weeks, the soybean shoots that produced healthy, viable roots can be transferred to soil. The soybean shoots comprising healthy, viable roots can be placed in soil which is contained in an open plastic sundae cup. The plastic sundae cups containing the transferred soybean shoots comprising roots can be placed in a CON-VIRON™ for acclimatization of soybean plantlets. The rooted soybean plantlets can be acclimated in the open sundae cups for several weeks before the plantlets are transferred to the greenhouse.

Incorporation of a section agent comprising 2,4-D in soybean tissue culture rooting medium can be tested to eliminate non-germline, chimeric soybean transformation events and escapes. Following *Agrobacterium*-mediated transformation of soybean (cv. Maverick) with a binary vector containing the aad-12 transgene, soybean shoots can be regenerated and cultured onto rooting medium which contains a selection agent comprising 2,4-D. The shoots can be observed for root development and shoots which produce viable, white roots can be further assayed for expression of transgene via microscopy. The roots can be further tested via molecular confirmation for presence of the transgene. Presence of an actively expressing transgene within developed roots is indicative that the $L_2/L_3$ tissue layers have been transformed, thereby resulting in soybean germline transformants. A correlation may be observed between transgene expression and viable, white root formation, wherein a significant majority of the viable, white roots express the transgene in root tissues.

These results may be comparable to soybean shoots cultured on rooting medium that does not contain a selection agent. The control conditions may not include a selection agent in the rooting medium, and may result in soybean shoots that produce healthy roots. However, only about 50% of the rooted plants may express the transgene in root tissues.

Conversely, when the non-germline or chimeric transformed shoots are transferred to rooting medium comprising a selection agent, the shoots may not develop roots or the few roots that develop may turn brown or black. The shoots that produce brown or black roots may not express the transgene in root tissues, thereby indicating that the germline tissues may not be transformed with the transgene. These results may indicate that non-germline soybean transformation events either do not form roots or develop brown/black roots when cultured in rooting medium comprising a selection agent. The non-germline transformed soybean shoots may not survive or maybe distinguished visually, as identified by the production of brown/black roots, and thus may be culled at the rooting medium selection stage of tissue culture.

While aspects of this invention have been described in certain embodiments, they can be further modified within the spirit and scope of this disclosure. This application is therefore intended to cover any variations, uses, or adaptations of embodiments of the invention using its general principles. Further, this application is intended to cover such departures from the present disclosure as come within known or customary practice in the art to which these embodiments pertain and which fall within the limits of the appended claims.

What is claimed is:

1. A method of selecting soybean germline transformants, the method comprising:
   a. transforming a population of cells of a soybean plant with a transgene, wherein the population of transformed cells comprises transformed germline cells and transformed non-germline cells;
   b. regenerating shoots from the population of transformed cells;
   c. isolating the shoots produced by the population of transformed cells;
   d. subjecting the isolated regenerated shoots to a selective rooting medium comprising glufosinate, wherein (i) the subjected isolated regenerated shoots produced by the transformed germline cells create viable roots, and (ii) the subjected isolated regenerated shoots produced by the transformed non-germline cells do not create viable roots; and
   e. selecting soybean germline transformants based on the ability of the selected transformants to create viable roots in the glufosinate-containing rooting medium.

2. The method of claim 1, wherein the transforming employs a transformation method elected from the group consisting of *Agrobacterium* transformation, biolistics, calcium phosphate transformation, polybrene transformation, protoplast fusion transformation, electroporation transformation, ultrasonic transformation, liposome transformation, microinjection transformation, naked DNA transformation, plasmid vector transformation, viral vector transformation, silicon carbide mediated transformation, aerosol beaming transformation, or PEG transformation.

3. The method of claim 1, wherein the population of cells of a soybean plant comprises a soybean plant tissue.

4. The method of claim 3, wherein the soybean plant tissue is a subepidermal or corpus (L2/L3) tissue layer or an epidermal (L1) tissue layer.

5. The method of claim 4, wherein the L2/L3 tissue layer comprises a germline cell.

6. The method of claim 4, wherein the L1 tissue layer comprises a non-germline cell.

7. The method of claim 4, wherein the L2/L3 tissue layer is a meristematic soybean plant tissue, a root soybean plant tissue, or a vascular soybean plant tissue.

8. The method of claim 4, wherein the L1 tissue layer is a dermal soybean plant tissue, a ground soybean plant tissue, or a mantle soybean plant tissue.

9. The method of claim 1, wherein the transgene is contained within at least one gene expression cassette.

10. The method of claim 9, wherein the gene expression cassette comprises a selectable marker gene.

11. The method of claim 10, wherein the selectable marker gene is a phosphinothricin acetyl transferase gene.

12. The method of claim 9, wherein the gene expression cassette comprises a trait gene.

13. The method of claim 9, wherein the gene expression cassette comprises an RNAi gene.

14. The method of claim 1, wherein the selective rooting medium further comprises 2,4-Dichlorophenoxyacetic acid (2,4-D).

15. The method of claim 1, wherein the glufosinate concentration within the selective rooting medium is at least 1.0 mg/L.

16. The method of claim 1, wherein the glufosinate concentration in the selective rooting medium is from 1.0 mg/L to 10.00 mg/L.

17. The method of claim 1, wherein the glufosinate concentration in the selective rooting medium is 1.0 mg/L.

18. The method of claim 1, wherein the selective rooting medium comprises a basal salt, a vitamin, a mineral, and a carbon source.

19. The method of claim 18, wherein the basal salt is Gamborg's B-5 basal salt, Schenk & Hildebrandt basal salt, White's basal salt, Chu (N6) basal salt, DKW/Juglans basal salt, Hoagland's No. 2 basal salt, Murashige & Skoog basal salt, or a combination thereof.

20. The method of claim 19, wherein the basal salt is Murashige & Skoog basal salt.

21. The method of claim 18, wherein the vitamin is selected from the group consisting of Gamborg's B-5 vitamin, MEM vitamin, Murashige & Skoog vitamin, Schenk & Hildebrandt vitamin, and combinations thereof.

22. The method of claim 21, wherein the vitamin is Gamborg's B-5 vitamin.

23. The method of claim 18, wherein the carbon source is selected from the group consisting of glucose, dextrose, mannose, fructose, galactose, glucuronate, lactose, glycerol, and combinations thereof.

24. The method of claim 23, wherein the carbon source is sucrose.

25. The method of claim 14, wherein the 2,4-D concentration within the selective rooting medium is at least 2.0 mg/L.

* * * * *